(12) United States Patent
Moriya

(10) Patent No.: US 11,351,107 B2
(45) Date of Patent: Jun. 7, 2022

(54) EMULSIFIED COSMETIC

(71) Applicant: SHIN-ETSU CHEMICAL CO., LTD., Tokyo (JP)

(72) Inventor: Hiroyuki Moriya, Annaka (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 521 days.

(21) Appl. No.: 16/080,546

(22) PCT Filed: Feb. 24, 2017

(86) PCT No.: PCT/JP2017/007090
§ 371 (c)(1),
(2) Date: Aug. 28, 2018

(87) PCT Pub. No.: WO2017/187750
PCT Pub. Date: Nov. 2, 2017

(65) Prior Publication Data
US 2019/0015318 A1 Jan. 17, 2019

(30) Foreign Application Priority Data
Apr. 28, 2016 (JP) .............................. JP2016-90824

(51) Int. Cl.
| | | |
|---|---|---|
| *A61K 8/895* | (2006.01) | |
| *A61Q 19/00* | (2006.01) | |
| *A61K 8/81* | (2006.01) | |
| *A61K 8/891* | (2006.01) | |
| *A61Q 1/02* | (2006.01) | |
| *A61K 8/06* | (2006.01) | |

(52) U.S. Cl.
CPC .............. *A61K 8/895* (2013.01); *A61K 8/064* (2013.01); *A61K 8/066* (2013.01); *A61K 8/81* (2013.01); *A61K 8/891* (2013.01); *A61Q 1/02* (2013.01); *A61Q 19/00* (2013.01)

(58) Field of Classification Search
CPC ........ A61K 8/895; A61K 8/064; A61K 8/066; A61Q 19/00
See application file for complete search history.

(56) References Cited

U.S. PATENT DOCUMENTS

| | | | |
|---|---|---|---|
| 4,970,252 A | 11/1990 | Sakuta et al. | |
| 4,987,169 A | 1/1991 | Kuwata et al. | |
| 5,236,986 A | 8/1993 | Sakuta | |
| 6,086,862 A | 7/2000 | Dubief et al. | |
| 6,177,063 B1 | 1/2001 | Hutchins | |
| 2002/0061319 A1* | 5/2002 | Bernard .................. | A61Q 3/02 424/401 |
| 2002/0131948 A1* | 9/2002 | Toumi .................... | A61Q 19/08 424/70.12 |
| 2003/0199660 A1 | 10/2003 | Sakuta | |
| 2004/0234477 A1 | 11/2004 | Sakuta | |
| 2004/0253197 A1 | 12/2004 | Sakuta | |
| 2007/0237798 A1* | 10/2007 | Apostol ................. | A61K 8/416 424/401 |
| 2008/0175809 A1 | 7/2008 | Sakuta et al. | |
| 2010/0028391 A1 | 2/2010 | Okawa et al. | |
| 2010/0317555 A1 | 12/2010 | Araki et al. | |
| 2012/0272861 A1 | 11/2012 | Morimitsu et al. | |
| 2015/0216787 A1 | 8/2015 | Hori et al. | |
| 2017/0240677 A1* | 8/2017 | Akabane ............. | C08F 290/068 |

FOREIGN PATENT DOCUMENTS

| | | |
|---|---|---|
| CN | 104661645 A | 5/2015 |
| EP | 1038519 A1 | 9/2000 |
| JP | S61-212324 A | 9/1986 |
| JP | H05-093136 A | 4/1993 |
| JP | H06-055897 B2 | 7/1994 |
| JP | H06-060286 B2 | 8/1994 |
| JP | H06-247835 A | 9/1994 |
| JP | H09-136813 A | 5/1997 |
| JP | 2631772 B2 | 7/1997 |
| JP | H10-066856 A | 3/1998 |

(Continued)

OTHER PUBLICATIONS

Mar. 5, 2019 Office Action issued in Japanese Patent Application No. 2016-090824.

(Continued)

*Primary Examiner* — Nannette Holloman
(74) *Attorney, Agent, or Firm* — Oliff PLC

(57) ABSTRACT

The present invention provides an emulsified cosmetic, including: an anionic acryl silicone copolymer (A) having an acryl chain as the main chain, the copolymer including, as monomer units, (I) 1 to 30% by mass of a polymerizable hydrophilic monomer having carboxylic acid, phosphoric acid, or sulfonic acid neutralized with a base, and (II) 10% by mass or more of a silicone macromonomer represented by the following general formula (1), or a silicone dendron group-containing polymerizable monomer; an oil material (B); and water (C). Accordingly, the present invention provides an emulsified cosmetic having excellent emulsification stability and non-stickiness.

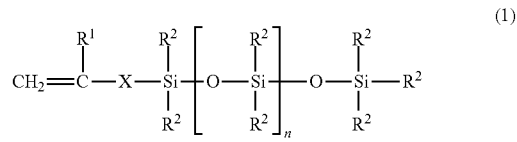

(1)

20 Claims, 1 Drawing Sheet

(56) References Cited

FOREIGN PATENT DOCUMENTS

| | | | |
|---|---|---|---|
| JP | H10-182356 A | 7/1998 | |
| JP | 2000-038325 A | 2/2000 | |
| JP | 2000-053554 A | 2/2000 | |
| JP | 2000-297027 A | 10/2000 | |
| JP | 2001-139414 A | 5/2001 | |
| JP | 2001-342255 A | 12/2001 | |
| JP | 2002-512943 A | 5/2002 | |
| JP | 2006-056861 A | 3/2006 | |
| JP | 2007-332295 A | 12/2007 | |
| JP | 2008-174504 A | 7/2008 | |
| JP | 2009-185144 A | 8/2009 | |
| JP | 2009-185296 A | 8/2009 | |
| JP | 2010-143833 A | 7/2010 | |
| JP | 2011-016733 A | 1/2011 | |
| JP | 2012-072081 A | 4/2012 | |
| JP | 2014-040512 A | 3/2014 | |
| WO | 03/020828 A1 | 3/2003 | |
| WO | 03/024413 A1 | 3/2003 | |
| WO | WO-2014030771 A2 * | 2/2014 | ............... A61Q 1/06 |

OTHER PUBLICATIONS

Nov. 25, 2019 Extended European Search Report issued in European Patent Application No. 17789039.9.
Oct. 1, 2019 Office Action issued in Japanese Patent Application No. 2016-090824.
Dec. 24, 2020 Office Action issued in Chinese Patent Application No. 201780026036.9.
Oct. 30, 2018 International Preliminary Report on Patentability issued in International Patent Application No. PCT/JP2017/007090.
Apr. 18, 2017 International Search Report issued in International Application No. PCT/JP2017/007090.
Kazuki Kageshima. "Carboxyl Hensei Silicone no Nyuka ni Okeru Kaimen Kasseizai Toshiteno Oyo" Fragrance Journal, 2005, special extra issue, No. 19, pp. 125-130.
Ichiro ONO. "Development of new cosmetics silicones for foundation purposes" Fragrance Journal, May 2000, pp. 65-70.

* cited by examiner

EMULSIFIED COSMETIC

TECHNICAL FIELD

The present invention relates to an emulsified cosmetic.

BACKGROUND ART

An oil material-containing composition needs emulsifying with surfactants, and the use of such surfactants including a silicone structure has been examined in various fields. One typical surfactant component is polyether-modified silicone or polyglycerin-modified silicone (Patent Documents 1 to 4). In addition, graft-type acryl silicone polymers having an acrylic structure as the main chain have widely been used as a film-forming agent (Patent Document 5). It is suggested that this type of silicone polymer can be used as a surfactant (Patent Documents 6 and 7).

However, the emulsified cosmetic using each of these silicone surfactants unfortunately fails to provide satisfactory emulsification stability, resulting in cosmetic separation and changes in feeling on use with time. Another problem of stickiness upon application has been demanded to be solved.

CITATION LIST

Patent Literature

Patent Document 1: Japanese Unexamined Patent Application Publication No. S61-212324
Patent Document 2: Japanese Unexamined Patent Application Publication No. H05-093136
Patent Document 3: Japanese Unexamined Patent Application Publication No. H10-066856
Patent Document 4: Japanese Unexamined Patent Application Publication No. 2000-053554
Patent Document 5: Japanese Unexamined Patent Application Publication No. H10-182356
Patent Document 6: Japanese Unexamined Patent Application Publication No. 2001-139414
Patent Document 7: Japanese Unexamined Patent Application Publication No. 2012-072081

SUMMARY OF INVENTION

Technical Problem

The present invention was made in view of the situation to solve the conventional problems with silicone surfactants used in emulsified cosmetics, and has an object to provide an emulsified cosmetic having excellent emulsification stability and non-stickiness.

Solution to Problem

To solve these problems, the present invention provides an emulsified cosmetic, including:
an anionic acryl silicone copolymer (A) having an acryl chain as the main chain, the copolymer including, as monomer units, at least
(I) 1 to 30% by mass of a polymerizable hydrophilic monomer having carboxylic acid, phosphoric acid, or sulfonic acid neutralized with a base, and
(II) 10% by mass or more of a silicone macromonomer represented by the following general formula (1), or a silicone dendron group-containing polymerizable monomer,

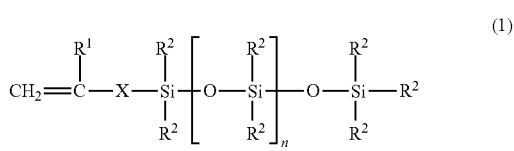

wherein, X represents a divalent aromatic group having 6 to 12 carbon atoms or —COOR$^3$—; R$^3$ represents an aliphatic group that is bonded to Si; R$^1$ represents a hydrogen atom or a methyl group; R$^2$ represents the same or different fluorine-substituted or unsubstituted monovalent alkyl group having 1 to 30 carbon atoms or aryl group; and "n" represents an integer of 1 to 100: an oil material (B); and
water (C).

Such an emulsified cosmetic provides excellent emulsification stability, favorable long lasting use, non-stickiness, and refreshing feeling on use.

In addition, the oil material (B) is preferably a silicone oil.
Accordingly, when the oil material (B) is a silicone oil, the emulsified cosmetic provides more favorable feeling on use.
In this case, the oil material (B) is preferably a polar oil.
In the present invention, the emulsified cosmetic can be in the form of a multiphase emulsion.
Accordingly, when the oil material (B) is a polar oil, the emulsified cosmetic obtained can be in the form of a multiphase emulsion.
Furthermore, the emulsified cosmetic preferably includes an aqueous system thickener (D).
The emulsified cosmetic including such an aqueous system thickener (D) can suppress separation of an emulsified product and provide refreshing feeling on use.
Furthermore, the emulsified cosmetic preferably includes a surfactant (E) other than the component (A).
The emulsified cosmetic, including such a surfactant (E) other than the component (A), provides more excellent usability.
Also, the silicone dendron group-containing polymerizable monomer is preferably selected from the following formulae,

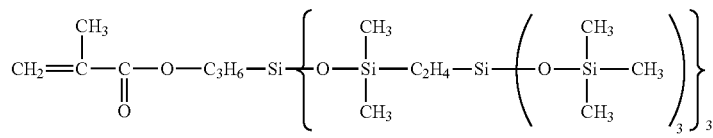

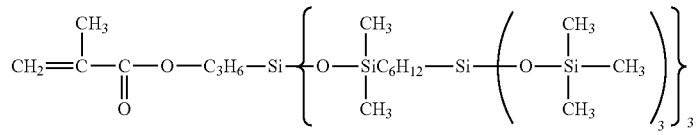

-continued
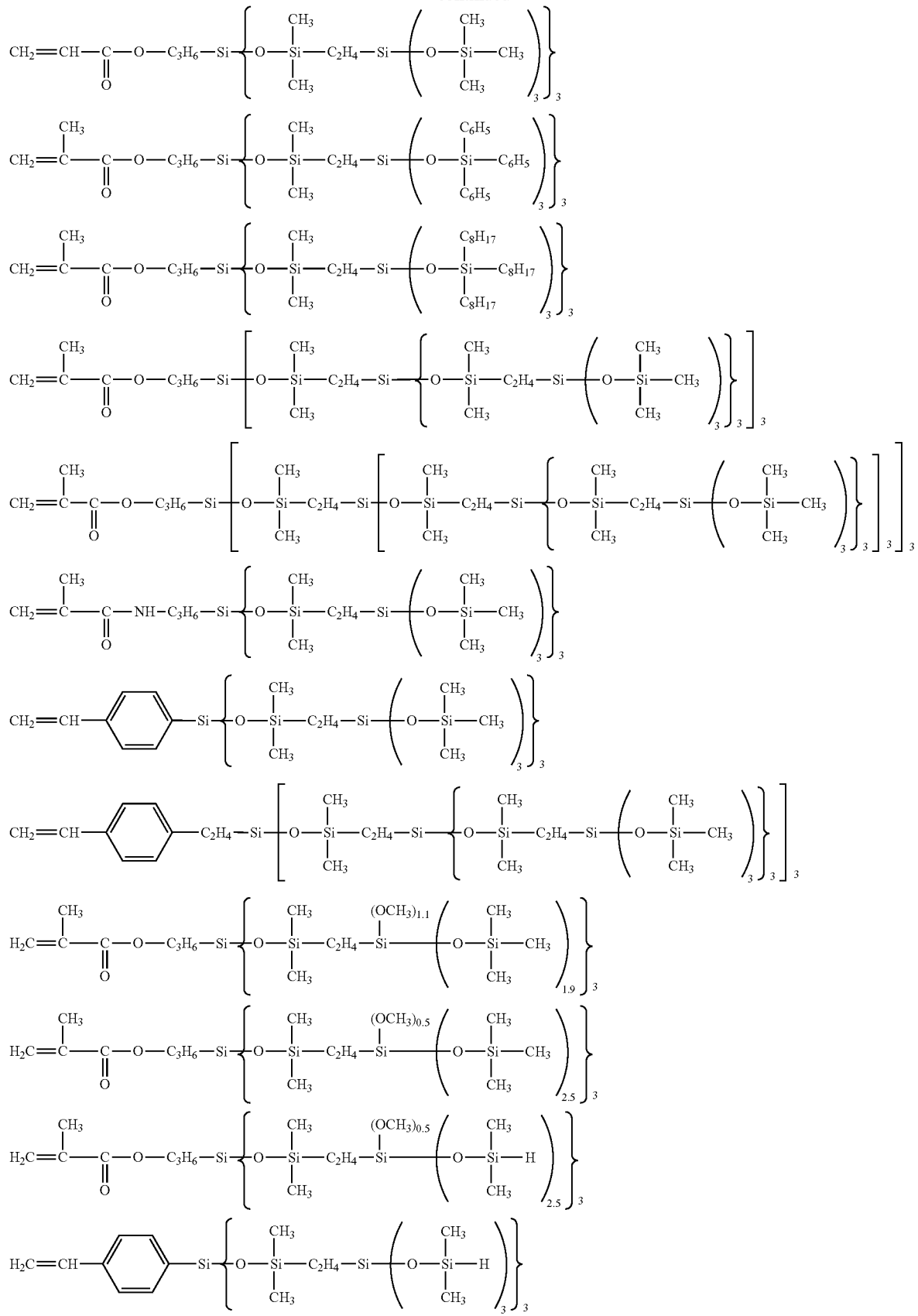

Accordingly, illustrative example of the silicone dendron group-containing polymerizable monomer of the monomer unit (II) includes silicone dendron group-containing polymerizable monomers selected from the formulae.

Advantageous Effects of Invention

The component (A) used in the present invention can stably emulsify various types of oil materials to provide an emulsified cosmetic having excellent emulsification stability, and the emulsified cosmetic containing such components (A) to (C) has excellent emulsification stability, favorable long lasting use, non-stickiness, and refreshing feeling on use. When a polar oil in particular is used as a component (B), the resulting emulsified cosmetic can be in the form of a multiphase emulsion. Although the production of multiphase emulsions normally requires multi-step emulsification; the multiphase emulsion in the present invention can be obtained by a single emulsification step.

DESCRIPTION OF EMBODIMENTS

Figure 1:
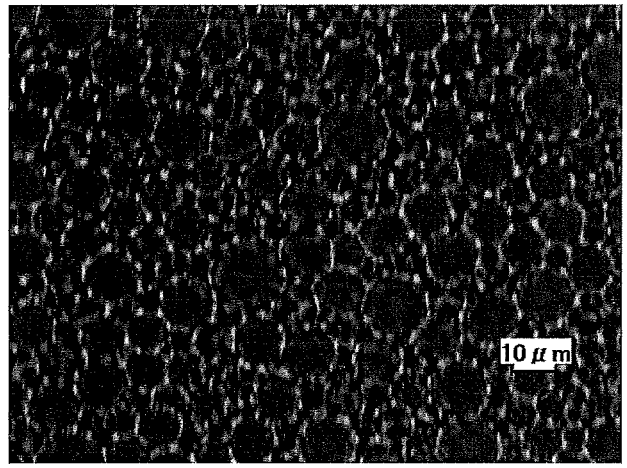
FIG. 1 is a micrograph illustrating a W/O emulsion of a cream of Example 1.

Inventors of the present invention have carried out an extended investigation and found that the emulsified cosmetic containing the following components (A) to (C) provides excellent emulsification stability, favorable long lasting use, non-stickiness, and refreshing feeling on use. In particular, the effect of excellent emulsification stability can be provided in that carboxylic acid, phosphoric acid, or sulfonic acid of a hydrophilic group in the component (A) as a surfactant is neutralized with a basic substance, and a silicone is grafted in an acrylic polymer at random. Based on that information, the present invention was accomplished.

Specifically, the present invention provides an emulsified cosmetic, including:
an anionic acryl silicone copolymer (A) having an acryl chain as the main chain, the copolymer including, as monomer units, at least
(I) 1 to 30% by mass of a polymerizable hydrophilic monomer having carboxylic acid, phosphoric acid, or sulfonic acid neutralized with a base, and
(II) 10% by mass or more of a silicone macromonomer represented by the following general formula (1), or a silicone dendron group-containing polymerizable monomer,

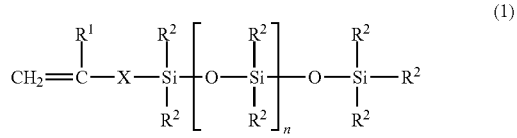

(1)

wherein, X represents a divalent aromatic group having 6 to 12 carbon atoms or —COOR$^3$—; R$^3$ represents an aliphatic group that is bonded to Si; R$^1$ represents a hydrogen atom or a methyl group; R$^2$ represents the same or different fluorine-substituted or unsubstituted monovalent alkyl group having 1 to 30 carbon atoms or aryl group; and "n" represents an integer of 1 to 100: an oil material (B); and
water (C).
The components (A) to (C), and other components will be described in detail.
(A) Anionic Acryl Silicone Copolymer
The component (A) in the present invention is an anionic acryl silicone copolymer including, as monomer units, at least (I) 1 to 30% by mass of a polymerizable hydrophilic monomer having carboxylic acid, phosphoric acid, or sulfonic acid neutralized with a base, and (II) 10% by mass or more of a silicone macromonomer represented by the following general formula (1), or a silicone dendron group-containing polymerizable monomer, having an acryl chain as the main chain, and having an acryl structure as the main chain and a structure in which a silicone is grafted at random.
(I) Polymerizable Hydrophilic Monomer Having Carboxylic Acid, Phosphoric Acid, or Sulfonic Acid Neutralized with a Base The component (A) in the emulsified cosmetic of the present invention includes, as a monomer unit (I), a structural unit in which a polymerizable hydrophilic monomer having carboxylic acid, phosphoric acid, or sulfonic acid is neutralized with a base.

The polymerizable hydrophilic monomer containing carboxylic acid may be a carboxylic acid-containing vinyl-type monomer such as (meth)acrylic acid, itaconic acid, crotonic acid, fumaric acid, and maleic acid, preferably (meth)acrylic acid and itaconic acid, and more preferably (meth)acrylic acid.

Illustrative example of the phosphoric acid-containing polymerizable hydrophilic monomer includes acid phosphoxyethyl methacrylate, 3-chloro-2-acid phosphoxy propyl methacrylate, acid phosphoxy propyl methacrylate, acid phosphoxyethyl acrylate, acid phosphoxypolyoxy ethyleneglycol monomethacrylate, acid phosphoxy polyoxypropylene glycol monomethacrylate, methacrylamide phosphonate, acrylamide phosphonate, methacrylamide diphosphonate, and acrylamide diphosphonate, preferably acid phosphoxyethyl methacrylate, acid phosphoxy propyl methacrylate, acid phosphoxyethyl acrylate, acid phosphoxypolyoxy ethyleneglycol monomethacrylate, and acid phosphoxy polyoxypropylene glycol monomethacrylate.

Illustrative example of the sulfonic acid-containing polymerizable hydrophilic monomer includes vinyl sulfonic acid, p-styrene sulfonic acid, (meth)acrylic acid butyl-4-sulfonic acid, (meth)acryloxy benzene sulfonic acid, and 2-acrylamide-2-methylpropane sulfonic acid, preferably vinyl sulfonic acid, p-styrene sulfonic acid and 2-acrylamide-2-methylpropane sulfonic acid, and particularly preferably 2-acrylamide-2-methylpropane sulfonic acid, but the sulfonic acid group-containing unsaturated monomer that can be used in the present invention is not restricted thereto.

The amount of these polymerizable hydrophilic monomer-derived monomer units is 1 to 30% by mass in an anionic acryl silicone copolymer. When the amount is less than 1% by mass or exceeds 30% by mass, a stable emulsified product cannot be obtained.

The emulsified cosmetic of the present invention contains these polymerizable hydrophilic monomers in the state that the acid sites of the polymerizable hydrophilic monomers are neutralized with a basic substance. When such neutralization doesn't occur, an emulsion having high emulsification stability cannot be obtained. The basic substance is not particularly restricted to the following substances so long as it forms a salt, but may be a basic compound containing an alkali metal or an alkaline earth metal, or an amine compound. Preferably, sodium hydroxide, sodium hydrogen carbonate, sodium carbonate, sodium hydride, sodium alkoxide, potassium hydroxide, potassium hydrogen carbonate, potassium carbonate, potassium alkoxide, diethyl amine, triethyl amine, 2-ethylhexyl amine, 3-methoxypropyl amine, 3-ethoxypropyl amine, diisobutyl amine, monoethanol amine, diethanol amine, triethanol amine, isopropyl amine, diisopropyl amine, isopropanol amine, N,N-diisopropanol amine, 2-amino-2-methyl-1-propanol, 2-(dimethyl amino)-2-methyl propanol, N,N-dimethyl ethanol amine, N,N-diethyl ethanol amine, N,N-dibutyl ethanol amine, N-(2-amino ethyl)ethanol amine, N-methyl diethanol amine, N-methyl ethanol amine, 3-amino-1-propanol, morpholine, and n-methyl morpholine may be used.

(II) Silicone Macromonomer Represented by the Following General Formula (1), or Silicone Dendron Group-Containing Polymerizable Monomer The component (A) in the emulsified cosmetic of the present invention includes, as a monomer unit (II), a structural unit of a silicone macromonomer represented by the following general formula (1), or a silicone dendron group-containing polymerizable monomer.

The silicone macromonomer represented by the following formula (1)-derived structural unit, or the silicone dendron group-containing polymerizable monomer-derived structural unit is a lipophilic group to enhance the solubility to each type of oil material. The grafted silicone chain stably exists in an oil phase in the emulsified product to enhance the emulsification stability.

The silicone macromonomer in the monomer unit (II) is represented by the following general formula (1),

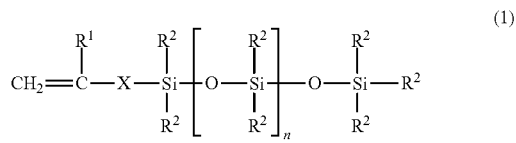

wherein, X represents a divalent aromatic group having 6 to 12 carbon atoms or $-COOR^3-$; $R^3$ represents an aliphatic group that is bonded to Si; $R^1$ represents a hydrogen atom or a methyl group; $R^2$ represents the same or different fluorine-substituted or unsubstituted monovalent alkyl group having 1 to 30 carbon atoms or aryl group; and "n" represents an integer of 1 to 100.

The $R^1$ of the silicone macromonomer represented by the formula (1) represents a hydrogen atom or a methyl group, preferably a methyl group.

Also, $R^2$ represents the same or different fluorine-substituted or unsubstituted monovalent alkyl group having 1 to 30 carbon atoms or aryl group, but more preferable to the skin is a fluorine-substituted or an unsubstituted monovalent alkyl group having carbon atoms 1 to 6, or an aryl group. A methyl group, a phenyl group, or a trifluoropropyl group is more preferable in view of hypoallergenic property to the skin and slipperiness, and a methyl group is most preferable.

X represents a divalent aromatic group having 6 to 12 carbon atoms or $-COOR^3-$, preferably a divalent aromatic group having carbon atoms 6 to 8 or $-COOR^3-$. Illustrative example of the divalent aromatic group includes a phenylene group, a tolylene group, a xylylene group, and a mesitylene group, preferably a phenylene group. In the $-COOR^3-$, $R^3$ represents an aliphatic group that is bonded to Si, and the carbonyl group is bonded to a carbon atom of the main chain of a copolymer. $R^3$ represents e.g., $-(CH_2)_a-$, and herein, "a" represents an integer of 1 to 9, preferably an integer of 2 to 7, and more preferably an integer of 3 to 5.

"n" represents an integer of 1 to 100, preferably an integer of 3 to 80, more preferably an integer of 5 to 65. When "n" exceeds an upper limit of 100, the reactivity in the polymerization reaction in the component (A) copolymer production can be reduced.

Illustrative example of the silicone dendron monomer of (II) includes the following formulae,

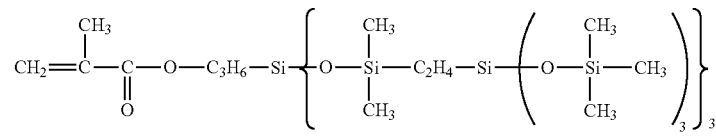

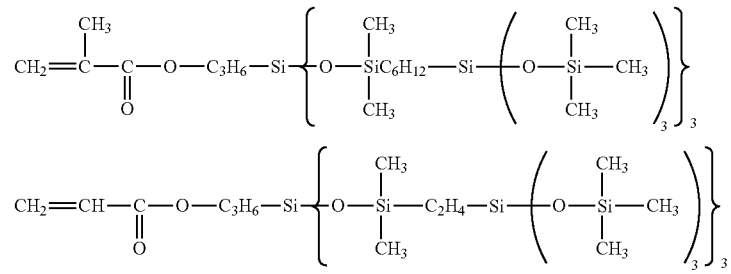

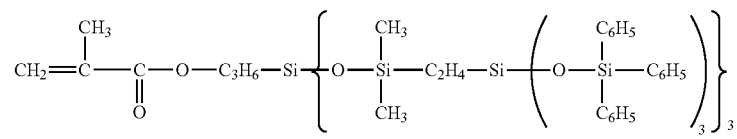

-continued

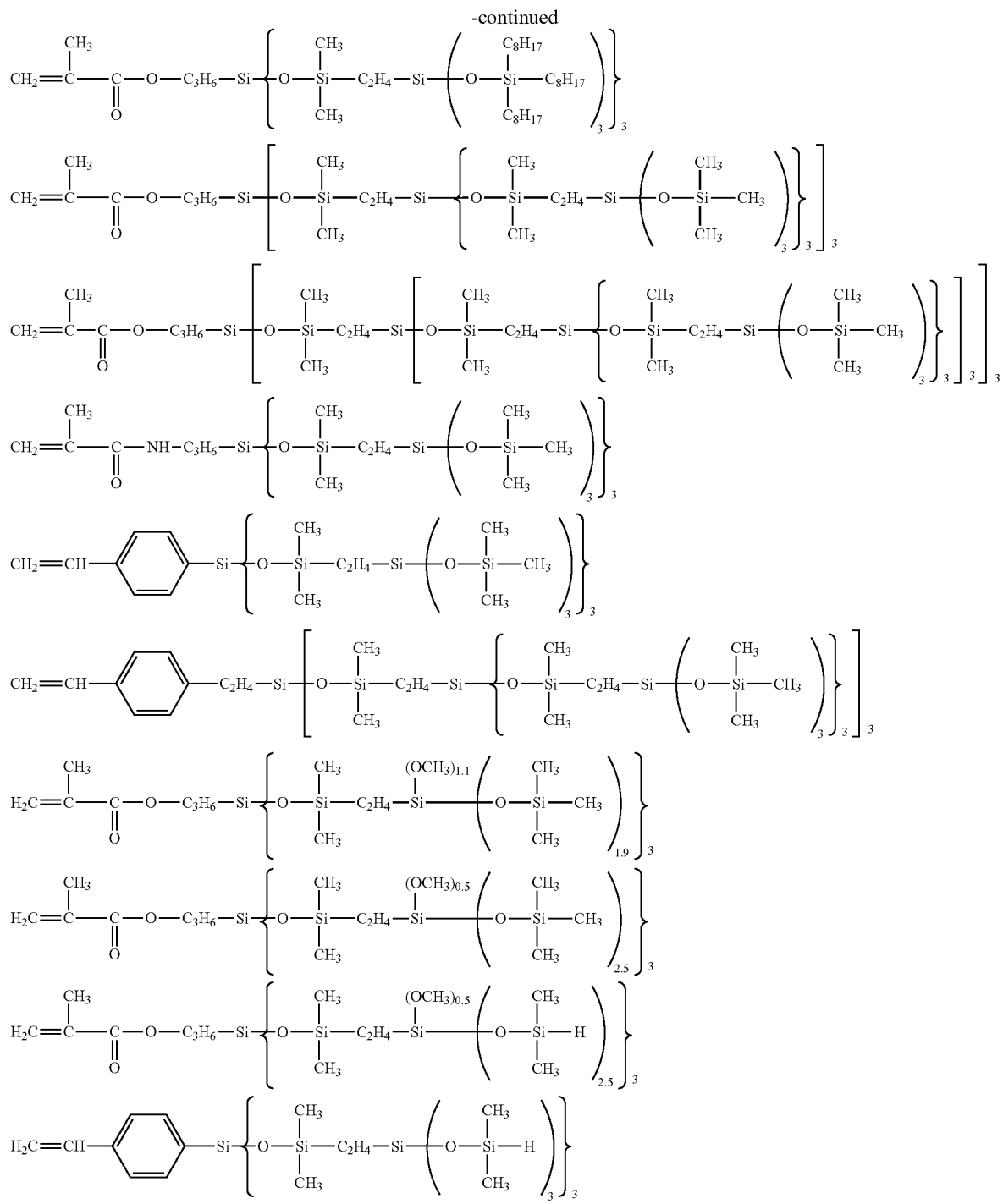

A silicone macromonomer represented by the general formula (1)-derived monomer unit, or a silicone dendron group-containing polymerizable monomer-derived monomer unit is contained by 10% by mass or more in an anionic acryl silicone copolymer, preferably 10% by mass or more and 70% by mass or less.

Other monomer unit components constituting the component (A) may be the one having a radical polymerizable vinyl group, and illustrative example of the vinyl monomer includes lower alkyl (meth)acrylate such as (meth)acrylic acid methyl, (meth)acrylic acid ethyl, (meth)acrylic acid n-propyl, (meth)acrylic acid isopropyl, (meth)acrylic acid n-butyl, (meth)acrylic acid isobutyl, (meth)acrylic acid tert-butyl, (meth)acrylic acid n-hexyl, and (meth)acrylic acid cyclohexyl; higher alkyl (meth) acrylate such as (meth) acrylic acid-2-ethylhexyl, (meth)acrylic acid octyl, (meth) acrylic acid lauryl, and (meth)acrylic acid stearyl; fatty acid vinyl ester such as vinyl acetate, vinyl propionate, vinyl butyrate, vinyl caproate, 2-ethylhexanoate vinyl, vinyl laurate, and stearic acid vinyl; an aromatic group-containing monomer such as styrene, vinyltoluene, benzyl (meth) acrylate, and phenoxyethyl(meth) acrylate; an amide group-containing vinyl monomer such as (meth)acrylamide, N-methylol (meth) acrylamide, N-methoxymethyl(meth) acrylamide, isobutoxymethoxy(meth)acrylamide, N,N-dimethyl(meth)acrylamide, vinyl pyrrolidone, and N-vinyl acetamide; a hydroxyl group-containing vinyl monomer such as (meth)acrylic acid hydroxyethyl, (meth)acrylic acid hydroxy propyl, glyceryl(meth) acrylate, and hydroxyethyl acrylamide; ether bond-containing vinyl monomer such as tetrahydrofurfuryl (meth) acrylate, butoxyethyl(meth) acrylate, ethoxy diethylene glycol(meth) acrylate, polyethylene glycol (meth) acrylate, polypropylene glycol mono (meth) acrylate, hydroxy butylvinylether, cetyl vinylether, and 2-ethylhexylvinylether; (meth)acrylic acid glycidyl, (meth)acrylic glycidylether, and methacryloyloxy ethyl isocyanate.

A multifunctional vinyl monomer can also be used, and illustrative example thereof includes trimethylol propane tri(meth) acrylate, pentaerythritol tri(meth) acrylate, ethylene glycol di(meth) acrylate, tetraethylene glycol di(meth) acrylate, polyethylene glycol di(meth) acrylate, 1,4-butanediol di(meth) acrylate, 1,6-hexane diol di(meth) acrylate, neopentyl glycol di(meth) acrylate, trimethylol propane tri-oxy ethyl(meth) acrylate, tris(2-hydroxyethyl)isocyanurate di(meth) acrylate, tris(2-hydroxyethyl)isocyanurate tri(meth) acrylate, and an unsaturated group-containing silicone compound such as polydimethylsiloxane blocked with a styryl group(s).

The polymerization for manufacturing the component (A) can occur in the presence of the monomer and the radical polymerization initiator such as benzoyl peroxide, lauroyl peroxide, and azobisisobutyronitrile. The method of polymerization may be any of solution polymerization method, emulsion polymerization method, suspension polymerization method, or bulk polymerization process. Among them, the solution polymerization method is preferable in that dispersion of a graph of Gel Permeation Chromatography (GPC) to examine the weight average molecular weight obtained and the weight average molecular weight of a copolymer are readily adjusted accordingly. Illustrative example of the solvent used in polymerization includes an aliphatic organic solvent such as pentane, hexane, decane, dodecane, hexadecane, and octadecane; an aromatic organic solvent such as benzene, toluene, and xylene; an alcohol-based organic solvent such as methanol, ethanol, propanol, butanol, hexanol, and decanol; a halogenated organic solvent such as chloroform, and carbon tetrachloride; and a ketone-based organic solvent such as acetone and methyl ethyl ketone, and polymerization reaction may be performed in an organic solvent. However, solventless, ethanol, or isopropanol is preferably be used in view of cosmetic use.

The component (A) contained in the emulsified cosmetic of the present invention contains, as an monomer unit, a polymerizable hydrophilic monomer while the acid site (carboxylic acid, phosphoric acid, or sulfonic acid) of the polymerizable hydrophilic monomer is neutralized with a basic substance. Such neutralization may occur by allowing a base to react with a copolymer before preparing an emulsified cosmetic, or by mixing a copolymer and a base when an emulsified cosmetic is prepared.

The weight average molecular weight in terms of polystyrene of the component (A) thus manufactured in GPC is preferably 700 to 300,000, particularly preferably 5000 to 200,000, and much more preferably 8000 to 100,000.

(B) Oil Material

The emulsified cosmetic of the present invention contains one, two or more types of oil materials (B). The oil material (B) can be in any form of a solid, a semi-solid, or a liquid used in a usual cosmetic.

Illustrative example of the silicone oil of the oil material (B) used in the present invention includes low viscous to high viscous linear or branched organopolysiloxanes such as dimethyl polysiloxane, caprylyl methicone, phenyl trimethicone, methyl phenyl polysiloxane, methylhexyl polysiloxane, methyl hydrogen polysiloxane, and dimethylsiloxane/methylphenylsiloxane copolymer; a cyclic organopolysiloxane such as octamethyl cyclotetrasiloxane, decamethyl cyclopentasiloxane, dodecamethyl cyclohexasiloxane, tetramethyl tetrahydrogen cyclotetrasiloxane, and tetramethyltetraphenyl cyclotetra siloxane; a branched organopolysiloxane such as tristrimethylsiloxy methylsilane and tetrakistri methylsiloxysilane; an amino-modified organopolysiloxane; a silicone rubber such as a gum dimethyl polysiloxane with a high degree of polymerization, gum amino-modified organopolysiloxane, gum dimethylsiloxane/methylphenylsiloxane copolymer; cyclic organopolysiloxane solution of a silicone gum and rubber, a trimethylsiloxysilicate, a trimethylsiloxysilicate cyclic organopolysiloxane solution, and a higher alkoxy-modified silicone such as stearoxysilicone; a higher fatty acid-modified organopolysilicone, an alkyl-modified organopolysilicone, a long chain alkyl-modified organopolysilicone, a fluorine-modified organopolysilicone, a silicone resin and a melt of a silicone resin. The amount of a silicone oil to be used is 1 to 60% by mass, preferably 3 to 40% by mass, and more preferably 5 to 30% by mass. Other oil materials that can allow for use in cosmetics may also be used.

Illustrative example of the polar oil includes diisobutyl adipate, 2-hexyldecyl adipate, di-2-heptylundecyl adipate, an N-alkylglycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyl dodecyl gum ester, oleyl oleate, octyldodecyl oleate, decyl oleate, neopentyl glycol dioctanoate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isononyl isononanoate, isotridecyl isononanoate, isopropyl palmitate, 2-ethylhexyl palmitate, 2-hexyldecyl palmitate, 2-heptylundecyl palmitate, cholesteryl 12-hydroxystearate, a dipentaerythritol fatty acid ester, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate ester, isopropylester lauroyl sarcosinate, and diisostearyl malate. Illustrative example of the glyceride oil includes acetoglyceryl, glyceryl triisooctanoate, glyceryl triisostearate, glyceryl triisopalmitate, glyceryl monostearate, glyceryl di-2-heptylundecanoate, glyceryl trimyristate, and diglyceryl myristate isostearate. Further, an avocado oil, a linseed oil, an almond oil, an insects wax, a perilla oil, an olive oil, a cacao butter, a kapok wax, a kaya oil, a carnauba wax, a lever oil, a candelilla wax, a purified candelilla wax, a beef tallow, a neats-foot oil, a beef bone fat, a cured beef tallow, an apricot kernel oil, a whale wax, a hydrogenated oil, a wheat germ oil, a sesame oil, a rice germ oil, a rice bran oil, a sugarcane wax, a sasanqua oil, a safflower oil, a shea butter, a Chinese tung oil, a cinnamon oil, a jojoba wax, a squalane oil, a squalene oil, a shellac wax, a turtle oil, a soybean oil, a tea seed oil, a camellia oil, an evening primrose oil, a corn oil, a pig fat, a rapeseed oil, a Japanese tung oil, a bran wax, a germ oil, a horse wax, a Persic oil, a palm oil, a palm kernel oil, a castor oil, a cured castor oil, a methyl ester of castor oil fatty acid, a sunflower oil, a grape seed oil, a bayberry wax, a jojoba oil, a hydrogenated jojoba oil, a macadamia nut oil, a bees wax, a mink oil, a meadow foam oil, a cotton seed oil, a cotton wax, a Japan wax, a Japan wax kernel oil, a montan wax, a coconut oil, a cured coconut oil, a tri-coconut oil fatty acid glyceride, a mutton tallow, a peanut oil, lanolin, liquid lanolin, reduced lanolin, lanolin alcohol, hard lanolin, lanolin acetate, lanolin alcohol acetate, isopropyl lanolin fatty acid, POE lanolin alcohol ether, POE lanolin alcohol acetate, polyethylene glycol lanolin fatty acid, POE hydrogenated lanolin alcohol ether, and an egg-yolk oil; lauric acid, a myristic acid, a palmitic acid, a stearic acid, a behenic acid, an undecylenic acid, an oleic acid, a linolic acid, a linolenic acid, an arachidonic acid, an eicosapentaenoic acid (EPA), a docosahexaenoic acid (DHA), an isostearic acid, a 12-hydroxystearic acid, a lauryl alcohol, a myristyl alcohol, a palmityl alcohol, a stearyl alcohol, a behenyl alcohol, a hexadecyl alcohol, an oleyl alcohol, an isostearyl alcohol, a hexyl dodecanol, an octyl dodecanol, a cetostearyl alcohol, a 2-decyl tetradecynol, a cholesterol, a phytosterol, a POE cholesterol ether, a monostearyl glycerin ether (batyl alcohol), and a monooleyl glyceryl ether (selachyl alcohol) are exemplified. Illustrative example of the organic UV-absorber includes a benzoic acid type UV-absorber such as para-amino benzoic acid; an anthranilic acid type UV-absorber such as methyl anthranilate; a salicylic type UV-absorber such as methyl salicylate; a cinnamic acid type UV-absorber such as octyl para-methoxy cinnamate; a benzophenone type UV-absorber such as 2,4-dihydroxybenzophenone; a urocanic acid type UV-absorber such as ethyl urocanate; and a dibenzoylmethane type UV-absorber such as 4-t-butyl-4'-methoxy-dibenzoylmethane. POE means polyoxyethylene. The amount of an ester oil to be used is 1 to 60% by mass, preferably 3 to 40% by mass, and more preferably 5 to 30% by mass. Other oil materials that can allow for use in cosmetics may also be used.

The use of a polar oil as an oil material obtains a multiphase emulsion. The multiphase emulsion can be obtained by stirring an oil-based component with a high shear mixer and adding a water-based component thereto, or stirring an oil-based component and a water-based component with a high shear mixer at the same time. Although, the production of multiphase emulsions normally requires multi-step emulsification; the multiphase emulsion obtained in the present invention can be obtained by a single emulsification step.

The emulsified cosmetic of the present invention may contain a hydrocarbon oil as an oil material (B). Illustrative example of the hydrocarbon oil includes a linear, a branched, and a volatile hydrocarbon oil, specifically an ozocerite, an α-olefin oligomer, a soft isoparaffin, an isododecane, a light liquid isoparaffin, a squalane, a synthetic squalane, a vegetable squalane, a squalene, a ceresin, a paraffin, a paraffin wax, a polyethylene wax, a polyethylene/polypropylene wax, a (ethylene/propylene/styrene) copolymer, a (butylene/propylene/styrene) copolymer, a liquid paraffin, a liquid isoparaffin, a pristane, a polyisobutylene, a hydrogenerated polyisobutene, a microcrystalline wax, and a Vaseline.

The emulsified cosmetic of the present invention contains water as a component (C). The emulsified cosmetic containing the components (A) to (C) provides excellent emulsification stability, favorable long lasting use, non-stickiness, and refreshing feeling on use.

The emulsified cosmetic of the present invention may include an aqueous system thickener (D).

Illustrative example thereof includes a plant polymer such as an Arabia gum, tragacanth, galactan, a carob gum, a guar gum, a karaya gum, carrageenan, pectin, agar, quince seed (marmelo), starch (rice, corn, potato, wheat, and so on), an algae colloid, a trant gum, a locust bean gum; a microbial polymer such as a xanthan gum, dextran, succinoglucan, and pullulan; an animal polymer such as collagen, casein, albumin, and gelatin; a starch polymer such as carboxymethyl starch and methyl hydroxypropyl starch; a cellulose polymer such as methyl cellulose, ethyl cellulose, methyl hydroxypropyl cellulose, carboxymethyl cellulose, hydroxymethyl cellulose, hydroxypropyl cellulose, nitrocellulose, sodium cellulose sulfate, sodium carboxymethyl cellulose, crystalline cellulose, and cellulose powder; an alginic acid polymer such as sodium alginate and propylene glycol alginate ester; a vinyl polymer such as polyvinyl methyl ether and carboxy vinyl polymer; a polyoxyethylene polymer; a polyoxyethylene polyoxypropylene copolymer; an acryl polymer such as sodium polyacrylate, polyethyl acrylate, polyacrylamide, and an acryloyldimethyl taurate salt copolymer; other synthetic water-soluble polymer such as polyethyleneimine and a cationic polymer; and a bentonite, aluminum magnesium silicate, montmorillonite, beidellite, nontronite, saponite, hectorite, anhydrous silicic acid, polyvinyl alcohol, and polyvinyl pyrrolidone. The emulsified cosmetic, including an aqueous system thickener, can suppress separation of an emulsified product to provide refreshing feeling on use. The amount thereof to be used is 0.1 to 15% by mass, preferably 0.1 to 10% by mass, and more preferably 0.5 to 5% by mass.

Furthermore, the emulsified cosmetic of the present invention can contain a surfactant (E) other than the component (A). The emulsified cosmetic of the present invention, depending on the purpose thereof, can use a surfactant to provide a cosmetic having more excellent usability. As to the surfactants like this, there are an anionic, a cationic, a nonionic and an amphoteric surfactant; and in the present invention, there is no particular restriction of the surfactant (E) other than the component (A) contained in the emulsified cosmetic of the present invention, and thus any of them may be used provided that the surfactant is used in a usual cosmetic.

Illustrative example of the anionic surfactant includes a fatty acid soap such as sodium stearate and triethanolamine palmitate, an alkyl ether carboxylic acid and a salt thereof, a condensate between an amino acid and a fatty acid, an alkane sulfonate, an alkene sulfonate, a sulfonate of a fatty acid ester, a sulfonate of a fatty acid amide, a sulfonate of a formalin condensate, an alkyl sulfate ester salt, a sulfate ester salt of a secondary alcohol, a sulfate ester salt of an alkyl and an allyl ether, a sulfate ester salt of a fatty acid ester, a sulfate ester salt of a fatty acid alkylolamide, a sulfate ester salt of a Turkey red oil and so on, an alkyl phosphate salt, an ether phosphate salt, an alkyl allyl ether phosphate salt, an amide phosphate salt, N-acyl lactate, N-acyl sarcosinate, and an N-acylamino acid activator; illustrative example of the cationic surfactant includes an alkyl amine salt, an amine salt such as a polyamine and an amino alcohol fatty acid derivative, an alkyl quaternary ammonium salt, an aromatic quaternary ammonium salt, a pyridinium salt, and an imidazolium salt.

Illustrative example of the nonionic surfactant includes a sorbitan fatty acid ester, a glycerin fatty acid ester, a polyglycerin fatty acid ester, a propylene glycol fatty acid ester, a polyethylene glycol fatty acid ester, a sucrose fatty acid ester, a methyl glycoside fatty acid ester, alkyl polyglucoside, a polyoxyethylene alkyl ether, a polyoxypropylene alkyl ether, a polyoxyethylene alkyl phenyl ether, a polyoxyethylene fatty acid ester, a polyoxyethylene sorbitan fatty acid ester, a polyoxyethylene sorbitol fatty acid ester, a polyoxyethylene glycerin fatty acid ester, a polyoxyethylene propylene glycol fatty acid ester, a polyoxyethylene castor oil, a polyoxyethylene hard castor oil, a polyoxyethylene phytostanol ether, a polyoxyethylene phytosterol ether, a polyoxyethylene cholestanol ether, a polyoxyethylene cholesterol ether, a linear or a branched polyoxyalkylene-modified organopolysiloxane, a linear or a branched organopolysiloxane co-modified with a polyoxyalkylene and an alkyl, a linear or a branched organopolysiloxane modified with a poly glycerin, a linear or a branched organopolysiloxane co-modified with a polyglycerin and an alkyl, an alkanol amide, a sugar ether, and a sugar amide.

Illustrative example of the amphoteric surfactant includes a betaine, an amino carboxylic acid salt, an imidazoline derivative, and an amido amine.

Among these surfactants, a linear or a branched organopolysiloxane having a polyoxyethylene chain in its molecular structure, a linear or a branched organopolysiloxane having a polyglycerin chain in its molecular structure, or alkyl comodified organopolysiloxane of each of the organopolysiloxanes are preferable. Commercially available product are not particularly restricted, but KF-6011, KF-6011P, KF-6043, KF-6012, KF-6013, KF-6015, KF-6016, KF-6017, KF-6028, KF-6028P, KF-6038, KF-6048, KF-6100, KF-6104, and KF-6105 (all products from Shin-Etsu Chemical Co., Ltd.) are preferable. A surfactant whose HLB is 2 to 10 is preferable, and the amount to be used is preferably 0.1 to 20% by mass, relative to the total amount of the emulsified cosmetic, and particularly preferably in the range of 0.2 to 10% by mass.

The emulsified cosmetic of the present invention may contain a powder. As to the powder, any powder may be used regardless of its form (spherical, needle-like, plate-like, and so on), its particle diameter (fumed, microparticle, pigment-class, and so on), and its particle structure (porous, non-porous, and so on), provided that the powder is used in a usual cosmetic. Illustrative example of the powder includes an inorganic powder, an organic powder, a surfactant metal salt powder, a coloring agent such as a color pigment, a pearl pigment, a metal powder pigment, a tar color, a natural color, and a dye.

Illustrative example of the inorganic powder includes titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, white mica, synthetic mica, golden mica, pink mica, black mica, lithia mica, silicic acid, anhydrous silicic acid, aluminum silicate, magnesium silicate, aluminum magnesium silicate, calcium silicate, barium silicate, strontium silicate, a metal tungstate salt, hydroxy apatite, vermiculite, higilite, bentonite, montmorillonite, hectorite, zeolite, ceramics powder, dibasic calcium phosphate, alumina, aluminum hydroxide, boron nitride, silica, and silica silylate.

Illustrative example of the organic powder includes a polyamide powder, a polyacrylic acid-acrylic ester powder, a polyester powder, a polyethylene powder, a polypropylene powder, a polystyrene powder, a polyurethane powder, a benzoguanamine powder, a polymethyl benzoguanamine powder, a tetrafluoroethylene powder, a polymethyl methacrylate powder, a cellulose powder, a silk powder, a nylon powder, a 12 nylon powder, a 6 nylon powder, a crosslinked spherical dimethylpolysiloxane fine powder having crosslinked dimethylpolysiloxane, a crosslinked spherical polymetylsilsesquioxane fine powder, fine powder obtained by coating crosslinked spherical organopolysiloxane rubber surface with polymetylsilsesquioxane particle, hydrophobic silica, a styrene-acrylic acid copolymer, a divinyl benzene-styrene copolymer, a vinyl resin, a urea resin, a phenol resin, a fluorinated resin, a silicone resin, an acryl resin, a melamine resin, an epoxy resin, a polycarbonate resin, a fine crystalline fiber powder, a starch powder, fatty acid starch derived powder, and lauroyl lysine.

Illustrative example of the surfactant metal salt powder (metal soap) includes zinc undecylenate, aluminum isostearate, zinc stearate, aluminum stearate, calcium stearate, magnesium stearate, zinc myristate, magnesium myristate, zinc cetylphosphate, calcium cetylphosphate, sodium cetylphosphate zinc, zinc palmitate, aluminum palmitate, and zinc laurate.

Illustrative example of the color pigment includes an inorganic red pigment such as iron oxide, iron hydroxide, and iron titanate; an inorganic brown pigment such as α-iron oxide; an inorganic yellow pigment such as a yellow iron oxide and a yellow earth; an inorganic black pigment such as a black iron oxide and a carbon black; an inorganic purple pigment such as a manganese violet and a cobalt violet; an inorganic green pigment such as chromium hydroxide, chromium oxide, cobalt oxide, and cobalt titanate; an inorganic blue pigment such as Prussian blue and azurite; a laked tar dye; a laked natural dye; and a synthetic resin powder obtained by hybridization of these powders.

Illustrative example of the pearl pigment includes a mica coated with titanium oxide, a mica coated with titanium oxide, oxychloro bismuth, oxychloro bismuth coated with titanium oxide, a talc coated with titanium oxide, a fish scale foil, and a color mica coated with titanium oxide; and illustrative example of the metal powder pigment includes an aluminum powder, a copper powder, and a stainless powder.

Illustrative example of the tar dye includes Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207; and the natural dye may be a powder selected from carminic acid, laccaic acid, carthamin, brazilin, and crocin.

Among these powders in the present invention are used a crosslinked spherical dimethylpolysiloxane fine powder having a structure at least whose part crosslinks dimethylpolysiloxane, a crosslinked spherical polymethyl silsesquioxane fine powder, a fine powder obtained by coating a crosslinked spherical polysiloxane rubber surface with a polymethyl silsesquioxane particle, a fine powder obtained by coating a crosslinked spherical diphenylpolysiloxane rubber surface with a polymethyl silsesquioxane particle, and a hydrophobized silica are preferable, and a powder having a fluorine group and a coloring agent are also used. Commercially available products thereof include KMP-590, KSP-100, KSP-101, KSP-102, KSP-105, and KSP-300 (all products from Shin-Etsu Chemical Co., Ltd.).

In addition, usable are a powder obtained by hybridizing, or treating these powders with a general oil material, a silicone oil, a fluorine-containing compound, a surfactant, and the like. These powders may or may not be surface-treated by a fluorine-containing compound treatment, a silicone resin treatment, pendant treatment, silane coupling agent treatment, titanium coupling agent treatment, an oil material treatment, N-acyl lysine treatment, polyacrylic acid treatment, metallic soap treatment, amino acid treatment, inorganic compound treatment, plasma treatment, and mechanochemical treatment beforehand. As required, one, two or more types thereof may be used. These powders are preferably used in an amount of 99% by mass or less, relative to the total amount of the emulsified cosmetic. In particular, the powder cosmetic is preferably used in an amount of 80 to 99% by mass, relative to the total amount of the emulsified cosmetic.

The emulsified cosmetic of the present invention may include a compound having an alcohol-based hydroxyl group in its molecular structure. Illustrative example of the compound includes a lower alcohol such as ethanol and isopropanol; a sugar alcohol such as sorbitol and maltose; a sterol such as cholesterol, sitosterol, phytosterol, and lanosterol; and a polyvalent alcohol such as butyleneglycol, propyleneglycol, dibutyleneglycol, and pentylene glycol, but normally a water-soluble monovalent alcohol and a water-soluble polyvalent alcohol are primarily used. The amount of the compound having an alcohol-based hydroxyl group in its molecular structure to be used is preferably in the range of 98% by mass or less, relative to the total amount of the emulsified cosmetic.

The emulsified cosmetic of the present invention may include a composition composed of a crosslinked organopolysiloxane polymer having no hydrophilic group and a liquid oil material. The crosslinked organopolysiloxane polymer is obtained by the reaction of an alkyl hydrogen polysiloxane and a crosslinking agent having a reactive vinyl unsaturated group at a chain end. Illustrative example of the alkyl hydrogen polysiloxane includes methyl hydrogen polysiloxane having a linear or a partial branch unit, and methyl hydrogen polysiloxane grafted with an alkyl chain having 6 to 20 carbon atoms. Two or more hydrogen atoms that are bonded to a silicon atom are required in a molecule on average. Illustrative example of the crosslinking agent includes those having two or more vinyl reaction sites in a molecule such as methyl vinylpolysiloxane and α,ω-alkenyl diene. These are shown in compositions disclosed in JP1925781B, JP1932769B, WO03-24413, and Japanese Unexamined Patent Application Publication No. 2009-185296. The crosslinked methylpolysiloxane is swollen with e.g., a low viscous silicone having 0.65 mm²/s (25° C.) to 100.0=²/s (25° C.), liquid paraffin, squalan, a hydrocarbon oil such as isododecane, and glyceride oil such as trioctanoin, and ester oil in an amount of the own weight or more. Commercially available products of the crosslinked organopolysiloxane are not particularly restricted, but KSG-15, KSG-16, KSG-18, KSG-1610, and USG-103 in the form of a paste with a silicone oil, and USG-106, KSG-41, KSG-42, KSG-43, KSG-44, and KSG-810 in the form of a paste with a hydrocarbon oil or a triglyceride oil (all products from Shin-Etsu Chemical Co., Ltd.) are preferable. The composition composed of the crosslinked organopolysiloxane having no such hydrophilic group and a liquid oil material are used preferably in an amount of 0.1 to 50% by mass, relative to the total amount of the emulsified cosmetic, more preferably 1 to 30% by mass.

The emulsified cosmetic of the present invention may further contain a composition composed of a hydrophilic crosslinked organopolysiloxane polymer and a liquid oil material. Preferable illustrative example of the hydrophilic group includes a polyether group and a polyglyceryl group. The crosslinked organopolysiloxane polymer having a polyether group and/or a polyglyceryl group is obtained by the reaction of an alkyl hydrogen polysiloxane and a crosslinking agent having a reactive vinyl unsaturated group at a chain end. Illustrative example of the alkyl hydrogen polysiloxane includes a methyl hydrogen polysiloxane grafted with a polyoxyethylene chain and a methyl hydrogen polysiloxane grafted with a polyglyceryl chain. Two or more hydrogen atoms that are bonded to a silicon atom are required in a molecule on average. Illustrative example of the crosslinking agent includes those having two or more vinyl reaction sites in a molecule such as methyl vinylpolysiloxane, α,ω-alkenyl diene, glycerol triallylether, polyoxyalkynylated glycerin triallylether, trimethylolpropanetriallyl ether, and polyoxyalkynylated trimethylolpropanetriallyl ether, and crosslinked products by the reaction of these substances may have at least one hydrophilic group. The compositions are preferably disclosed in Japanese patent No. 2631772, Japanese Unexamined Patent Application Publication No. H9-136813, Japanese Unexamined Patent Application Publication No. 2001-342255, WO03/020828, and Japanese Unexamined Patent Application Publication No. 2009-185296. The crosslinked organopolysiloxane polymer is swollen to a low viscous silicone having 0.65=²/s (25° C.) to 100.0=²/s (25° C.), liquid paraffin, squalan, a hydrocarbon oil such as isododecane, a glyceride oil such as trioctanoin, or an ester oil in an amount of the own weight or more. Commercially available products of crosslinked organopolysiloxane are not particularly restricted, but KSG-210, KSG-240, and KSG-710 in the form of a paste with a silicone oil, and KSG-310, KSG-320, KSG-330, KSG-340, KSG-820, KSG-830, and KSG-840 in the form of a paste with a hydrocarbon oil or a triglyceride oil (all products from Shin-Etsu Chemical Co., Ltd.) are preferable. The composition composed of the hydrophilic crosslinked organopolysiloxane and a liquid oil material are preferably used in an amount of 0.1 to 50% by mass, relative to the total amount of the cosmetic, more preferably in an amount of 1 to 30% by mass.

The emulsified cosmetic of the present invention may contain a silicone resin other than the component (A). Such a silicone resin is preferably selected from the group consisting of a silicone net-work compound including a $SiO_2$ unit and/or $RSiO_{1.5}$ (R represents an alkyl group), a linear acryl/silicone graft, and a block copolymer thereof. The linear acryl/silicone graft or the block copolymer may include at least one type selected from a pyrrolidone moiety, a long chain alkyl moiety, a polyoxyalkylene moiety, a fluoroalkyl moiety, and an anion moiety such as carboxylic acid. Commercially available products thereof are not particularly restricted, but KP-541, KP-543, KP-545, KP-549, KP-550, KP-571, KP-575, and KP-581, which is dissolved in a silicone oil, a hydrocarbon oil, or alcohol (all products from Shin-Etsu Chemical Co., Ltd.), are preferable.

The silicone net-work compound is preferably a silicone net-work compound represented as MQ, MDQ, MT, MDT, or MDTQ. M, D, T, and Q represent $R_3SiO_{0.5}$ unit, $R_2SiO$ unit, $RSiO_{1.5}$ unit, and $SiO_2$ unit, respectively. The silicone net-work compound may contain in one molecule at least one type selected from a pyrrolidone moiety, a long chain alkyl moiety, a polyoxyalkylene moiety, a fluoroalkyl moiety, and an amino moiety. Commercially available products thereof are not particularly restricted, but KF-7312J, KF-7312K, and KF-7312T (all products from Shin-Etsu Chemical Co., Ltd.) are preferable.

The silicone resin may be dissolved into a low viscous silicone oil, a volatile silicone oil, or other solvents. In each of these oils, the silicone resin is preferably used in an amount of 0.1 to 20% by mass, relative to the total amount of the emulsified cosmetic of the present invention, more preferably in an amount of 1 to 10% by mass.

The emulsified cosmetic of the present invention can include a silicone wax. The silicone wax is preferably a polylactone-modified polysiloxane to which polylactone as a ring opening polymer of a lactone compound of 5-membered ring or more is bonded. Alternatively, the silicone wax is preferably an acrylic-modified polysiloxane containing in one molecule at least one functional group selected from a pyrrolidone group, a long chain alkyl group, a polyoxyalkylene group, and a fluoroalkyl group. Commercially available products of a wax having a long chain alkyl group include KP-561P and KP-562P (all products from Shin-Etsu Chemical Co., Ltd.).

Alternatively, the silicone wax is preferably a silicone-modified olefin wax obtained by inducing an addition reaction of an olefin wax and an organohydrogen polysiloxane having one or more SiH bonds in one molecule. The olefin wax is obtained by copolymerizing ethylene and at least one type of diene, or copolymerizing ethylene and at least one type of olefin selected from α-olefins having carbon atoms 3 to 12, and at least one type of diene, and the diene is preferably vinyl norbornen.

When a silicone wax is used, regardless of which one to be selected, the amount thereof to be used is preferably 0.1 to 20% by weight, relative to the total amount of the emulsified cosmetic of the present invention, and particularly preferably 1 to 10% by weight.

The emulsified cosmetic of the present invention may be added with a component generally used in a usual cosmetic, an oil-soluble gelation agent (organic modified clay mineral), a resin, an antiperspirant, a moisturizer, an antibacterial-antiseptic agent, a fragrance, a salt, an antioxidant, a pH controller, a chelating agent, an algefacient, an anti-inflammatory agent, a skin care component (a skin-lightening agent, a cell activator, a rough skin-improver, a blood circulation promoter, a skin astringent agent, an antiseborrheic agent, and so on), a vitamin, an amino acid, a nucleic acid, a hormone, a clathrate compound, and a hair-immobilizing agent.

Illustrative example of the oil-soluble gelation agent is one, two or more types of gelation agents selected from a metal soap such as aluminum stearate, magnesium stearate, and zinc myristate; an amino acid derivative such as N-lauroyl-L-glutamic acid and α,γ-di-n-butyl amine; a dextrin fatty acid ester such as dextrin palmitate ester, dextrin stearate ester, and dextrin 2-ethylhexoate palmitate ester; a sucrose fatty acid ester such as sucrose palmitate ester and sucrose stearate ester; a fructo-oligosaccharide fatty acid ester such as fructo-oligosaccharide stearate ester and fructo-oligosaccharide 2-ethylhexanoate ester; benzylidene derivative of sorbitol such as monobenzylidene sorbitol and dibenzylidene sorbitol; an organic-modified clay mineral such as dimethyl benzyl dodecyl ammonium montmorillonite clay and dimethyl dioctadecyl ammonium montmorillonite clay.

Illustrative example of the antiperspirant is one, two or more types of antiperspirants selected from aluminum chlorohydrate, aluminum chloride, aluminum sesquichlorohydrate, zirconyl hydroxyl chloride, aluminum zirconium hydroxyl chloride, and an aluminum zirconium glycine complex.

Illustrative example of the moisturizer is one, two or more moisturizers selected from glycerin, sorbitol, propylene glycol, dipropylene glycol, 1,3-butylene glycol, pentylene glycol, glucose, xylitol, maltitol, polyethylene glycol, hyaluronic acid, chondroitin sulfate, pyrrolidone carboxylate salt, polyoxyethylene methyl glucoside, and polyoxypropylene methyl glucoside.

Illustrative example of the antibacterial-antiseptic agent is one, two or more types of antibacterial preservatives selected from para-oxybenzoate alkyl ester, benzoic acid, sodium benzoate, sorbic acid, potassium sorbate, and phenoxy ethanol, and illustrative example of the antibacterial agent is one, two or more types of antibacterial agents selected from benzoic acid, salicylic acid, carbolic acid, sorbic acid, a para-oxybenzoate alkyl ester, p-chloro-m-cresol, hexachlorophen, benzalkonium chloride, chlorhexidine chloride, trichlorocarbanilide, a photosensitive element, and phenoxy ethanol.

Illustrative example of the salt includes an inorganic salt, an organic salt, an amine salt and an amino acid salt. Illustrative example of the inorganic salt includes a potassium salt, a magnesium salt, a calcium salt, an aluminum salt, a zirconium salt, and a zinc salt of an inorganic acid such as hydrochloric acid, sulfuric acid, carbonic acid, and nitric acid, illustrative example of the organic salt includes a salt of an organic acid such as an acetic acid, dehydroacetic acid, citric acid, malic acid, succinic acid, ascorbic acid, and stearic acid, and illustrative example of the amine salt and amino acid salt includes a salt of an amine such as triethanol amine and a salt of amino acid such as a glutamic acid. In addition, a salt of hyaluronic acid and chondroitin sulfate, an aluminum zirconium glycine complex, and a neutralized salt obtained by neutralization of an acid and a base used in a cosmetic prescription can be used.

Illustrative example of the antioxidant includes tocopherol, butyl hydroxyl anisole, dibutyl hydroxyl toluene, and phytin, illustrative example of the pH controller includes lactic acid, citric acid, glycolic acid, succinic acid, tartaric acid, dl-malic acid, potassium carbonate, sodium bicarbonate, and ammonium bicarbonate, illustrative example of the chelating agent includes alanine, sodium edetate, sodium polyphosphate, sodium metaphosphate, and phosphoric acid, illustrative example of the algefacient includes L-menthol and camphor, and illustrative example of the anti-inflammatory agent includes one, two or more types of agents selected from allantoin, glycyrrhizinic acid and its salt, glycyrrhetic acid, stearyl glycyrrhetinate, tranexamic acid, and azulene.

Illustrative example of the skin care component is one, two or more types of skin care components selected from a skin-lightening agent such as a placenta extract, arbutin, glutathione, and a saxifrage extract; a cell activator such as a royal jelly, a photosensitive element, a cholesterol derivative, and an extract from hemolysed blood of a young calf; a rough-skin improver; a blood circulation promoter such as nonylic acid warenylamide, benzyl niconinate ester, β-butoxyethyl niconinate ester, capsaicin, zingerone, cantharides tincture, ichthammol, caffeine, tannic acid, α-borneol, niconic acid tocopherol, inositol hexanicotinate, cyclandelate, cinnarizine, tolazoline, acetyl choline, verapamil, cepharanthine, and γ-orizanol; a skin astringent agent such as zinc oxide and tannic acid; and an antiseborrheic agent such as sulfur and thianthol.

Illustrative example of the vitamin is one, two or more types of vitamins selected from a vitamin A such as a vitamin A oil, retinol, retinol acetate, and retinol palmitate; a vitamin B including a vitamin B2 such as riboflavin, riboflavin butyrate, and a flavin adenine nucleotide, a vitamin B6 such as pyridoxine hydrochloride salt, pyridoxine dioctanoate, and pyridoxine tripalmitate, a vitamin B12 and its derivative, and vitamin B15 and its derivative; a vitamin C such as L-ascorbic acid, L-ascorbic acid dipalmitate ester, sodium L-ascorbic-2-sulfate, and dicalcium L-ascorbic acid phosphate diester; a vitamin D such as ergocalciferol and cholecalciferol; a vitamin E such as α-tocopherol, β-tocopherol, γ-tocopherol, dl-α-tocopherol acetate, dl-α-tocopherol nicotinate, and dl-α-tocopherol succinate; a vitamin H; a vitamin P; a nicotinic acid such as nicotinic acid, benzyl nicotinate, and a nicotinic acid amide; a pantothenic acid such as calcium pantothenate, D-pantothenyl alcohol, pantothenyl ethyl ether, and acetyl pantothenyl ethyl ether; and biotin.

Illustrative example of the amino acids includes glycine, valine, leucine, isoleucine, serine, threonine, phenylalanine, arginine, lysine, aspartic acid, glutamic acid, cystine, cysteine, methionine, and tryptophan, illustrative example of the nucleic acid includes deoxyribonucleic acid, and illustrative example of the hormone is one, two or more types of hormones selected from estradiol and ethenyl estradiol.

As to the hair-immobilizing agent, an amphoteric polymer, an anionic polymer, a cationic polymer, and a nonionic polymer may be mentioned, and illustrative example of the hair-immobilizing polymer includes one or more of the hair-immobilizing agent selected from a polyvinyl pyrrolidine polymer such as a polyvinyl pyrrolidine and vinyl pyrrolidone/vinyl acetate copolymer; an acidic vinyl ether polymer such as a methyl vinyl ether/maleic anhydride alkyl half-ester copolymer; an acidic polyvinyl acetate polymer such as a vinyl acetate/crotonic acid copolymer; an acidic acryl polymer compound such as a (meta)acrylic acid/alkyl (meta)acrylate copolymer and a (meta)acrylic acid/alkyl (meta)acrylate/alkyl acrylamide copolymer; and an amphoteric acryl polymer such as an N-methacryloylethyl-N,N-dimethyl ammonium/α-N-methylcarboxybetaine/alkyl (meta)acrylate copolymer and hydroxypropyl (meta)acrylate/butylaminoethyl methacrylate/acrylic acid octyl amide copolymer. In addition, a polymer derived from a nature such as cellulose or its derivative, and keratin and collagen or a derivative thereof may be suitably used.

Illustrative example of the emulsified cosmetic of the present invention, with the above cosmetic components used, includes a skin care cosmetic such as a milky lotion, a cream, a cleansing cream, a pack, a massage material, a essence, a essence oil, a cleaner, a deodorant, a hand cream, a lip cream, and a wrinkle concealer; a make-up cosmetic such as a make-up foundation, a concealer, a white powder, and a liquid foundation; a hair cosmetic such as a shampoo, a rinse, a treatment, and a setting material; an antiperspirant; a UV-protective cosmetic such as a sunscreen oil, a sunscreen milky lotion, and a sunscreen cream.

EXAMPLE

The present invention will be described with reference to Synthesis Examples, and Examples and Comparative Examples of the emulsified cosmetic of the present invention, but the present invention is not restricted to the following Examples. Unless otherwise stated, the following "%" means "% by mass" of each component, relative to the total mass of 100%. The viscosity is measured at 25° C.

Synthesis Examples (1) to (6)

Isopropanol (140.0 g), each monomer shown in the following Table 1, and t-butyl peroxy-2-ethyl hexanoate (4.0 g) were fed into a glass flask equipped with a stirrer, a thermometer, and a reflux condenser, and the product was stirred in a stream of nitrogen and heated to reflux. After 5-hour polymerization, a volatile component was distilled under reduced pressure to obtain silicone copolymers (Synthesis Examples (1) to (6)). However, in Synthesis Example (3), an aqueous solution in which sodium hydroxide (0.6 g) was dissolved into purified water (5 g) was added before distilling a volatile component to neutralize a phosphate site. The silicone copolymers obtained in Synthesis Examples (1), (2), and (4) contain carboxylic acid and a sulfonic acid group, while the silicone copolymers obtained in Synthesis Examples (5) and (6) contain no carboxylic acid, phosphoric acid, or sulfonic acid. The number average molecular weight (in terms of polystyrene) was calculated by GPC.

TABLE 1

| | Synthesis Example of acryl silicone (g) | | | | | |
|---|---|---|---|---|---|---|
| | Synthesis Example (1) | Synthesis Example (2) | Synthesis Example (3) | Synthesis Example (4) | Synthesis Example (5) | Synthesis Example (6) |
| Acrylic acid | 10 | 15 | | | | |
| Acid phosphoxyethyl methacrylate | | | 3 | | | |
| 2-acrylamide-2-methylpropane sulfonic acid | | | | 4 | | |
| Silicone macromere (1) | 50 | | | 40 | 50 | |
| Silicone macromere (2) | | 30 | | | | 30 |
| Silicone dendron monomer | | | 60 | | | |
| Methyl methacrylate | 15 | 10 | 5 | 23 | 15 | 10 |
| Acrylic acid-2-ethylhexyl | 11 | | 12 | 10 | 11 | |
| (meth)acrylic acid isobutyl | 14 | 20 | 20 | 8 | 14 | 20 |
| (meth)acrylic acid n-stearyl | | 25 | | 15 | | 25 |
| 2-hydroxyethyl (meth) acrylate | | | | | 10 | |
| Methoxy polyethylene glycol (meth) acrylate | | | | | | 15 |

TABLE 1-continued

| | Synthesis Example of acryl silicone (g) | | | | | |
|---|---|---|---|---|---|---|
| | Synthesis Example (1) | Synthesis Example (2) | Synthesis Example (3) | Synthesis Example (4) | Synthesis Example (5) | Synthesis Example (6) |
| Number average molecular weight by GPC (TOSOH CORPORATION: in terms of polystyrene) | 17000 | 22000 | 20000 | 41000 | 15000 | 19000 |

Silicone macromere (1)

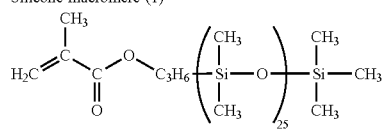

Silicone macromere (2)

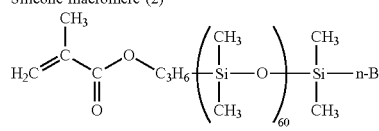

Silicone dendron monomer

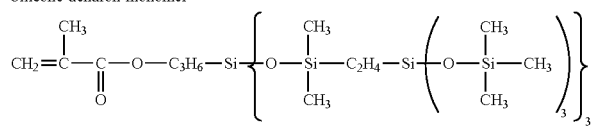

Examples 1 to 7, and Comparative Examples 1 to 7

The cream of the composition shown in the following Table 2 was prepared according to a conventional method (for adding a water-based component to an oil-based component). The cream obtained was subjected to sensory evaluation according to the following method. The results are shown in the following table.

[Sensory Evaluation Method]

The cream shown in the following Table 2 (2 g) was applied to the skin for good compatibility and was evaluated.

The refreshing feeling upon application, the non-stickiness after application, and the emulsion stability at 40° C. one month later were subjected to sensory evaluation. The results are shown by the following evaluation criteria by the number of panels saying "effective".

[Evaluation Criteria]

⊚: "Effective" from 4 to 5 panels
○: "Effective" from 3 panels
Δ: "Effective" from 2 panels
x: "Effective" from 1 panel or none

TABLE 2

| | | | Example | | | | | | |
|---|---|---|---|---|---|---|---|---|---|
| | | | 1 | 2 | 3 | 4 | 5 | 6 | 7 |
| 1 | Acryl Silicone in Synthesis Example 1 | | 2 | | | 2 | | | 2 |
| 2 | Acryl silicone in Synthesis Example 2 | | | 2 | | | 1.5 | | |
| 3 | Acryl silicone in Synthesis Example 4 | | | | 2 | | | 2 | |
| 4 | Acryl silicone in Synthesis Example 5 | | | | | | | | |

TABLE 2-continued

| # | Component | | | | | | | |
|---|---|---|---|---|---|---|---|---|
| 5 | Acryl silicone in Synthesis Example 6 | | | | | | | |
| 6 | KF-6017 *1 | | | | | | | |
| 7 | KF-6105 *2 | | | | | | | |
| 8 | Dimethyl polysiloxane (6 mm²/s) | 8 | 5 | 15 | | | | |
| 9 | Decamethyl cyclopentasiloxane | 12 | 20 | | 15 | 2 | 17 | 10 |
| 10 | Octyl para-methoxy cinnamate | | | | 5 | 18 | 3 | |
| 11 | Isotridecyl isononanoate | | | | | | | 10 |
| 12 | KF-6043 *3 | | | | | 2 | | |
| 13 | Carbopol 940 *4 | | | | 0.15 | 0.15 | 0.1 | 0.15 |
| 14 | 1,3-butylene glycol | 4 | 4 | 4 | 4 | 4 | 4 | 4 |
| 15 | Sodium hydroxide | 0.1 | 0.1 | | | 0.1 | 0.05 | |
| 16 | Triethanol amine | | | 0.3 | 0.3 | | 0.1 | 0.3 |
| 17 | Sodium chloride | 0.2 | 0.2 | 0.2 | 0.2 | 0.2 | 0.2 | 0.2 |
| 18 | Purified water | Remainder | Remainder | Remainder | Remainder | Remainder | Remainder | Remainder |
| Evaluation | Stability at 40° one month later | ◉ | ○ | ◉ | ◉ | ◉ | ○ | ◉ |
| | Refreshing feeling on use upon application | ◉ | ◉ | ○ | ◉ | ◉ | ◉ | ◉ |
| | Stickiness after application | ○ | ○ | ◉ | ◉ | ◉ | ○ | ◉ |
| | Form of emulsion | W/O | W/O | W/O | Multiphase | Multiphase | Multiphase | Multiphase |

| | | Comparative Example | | | | | | |
|---|---|---|---|---|---|---|---|---|
| | | 1 | 2 | 3 | 4 | 5 | 6 | 7 |
| 1 | Acryl Silicone in Synthesis Example 1 | 2 | | | | | | |
| 2 | Acryl silicone in Synthesis Example 2 | | | 1.5 | | | | |
| 3 | Acryl silicone in Synthesis Example 4 | | 2 | | | | | |
| 4 | Acryl silicone in Synthesis Example 5 | | | | | | 2 | |
| 5 | Acryl silicone in Synthesis Example 6 | | | | | | | 1.5 |
| 6 | KF-6017 *1 | | | | 2 | | | |
| 7 | KF-6105 *2 | | | | | 2 | | |

TABLE 2-continued

| | | | | | | | | |
|---|---|---|---|---|---|---|---|---|
| 8 | Dimethyl polysiloxane (6 mm²/s) | 8 | | | 8 | 5 | | |
| 9 | Decamethyl cyclopentasiloxane | 12 | 17 | 2 | 12 | 20 | 15 | 2 |
| 10 | Octyl para-methoxy cinnamate | | 3 | 18 | | | 5 | 18 |
| 11 | Isotridecyl isononanoate | | | | | | | |
| 12 | KF-6043 *3 | | | 2 | | | | 2 |
| 13 | Carbopol 940 *4 | | 0.1 | 0.15 | | | 0.15 | 0.15 |
| 14 | 1,3-butylene glycol | 4 | 4 | 4 | 4 | 4 | 4 | 4 |
| 15 | Sodium hydroxide | | | | | 0.1 | | 0.1 |
| 16 | Triethanol amine | | | | | | 0.3 | |
| 17 | Sodium chloride | 0.2 | 0.2 | 0.2 | 0.2 | 0.2 | 0.2 | 0.2 |
| 18 | Purified water | Remainder | Remainder | Remainder | Remainder | Remainder | Remainder | Remainder |
| Evaluation | Stability at 40° one month later | Δ | Δ | Δ | ○ | ○ | Δ | Δ |
| | Refreshing feeling on use upon application | ○ | Δ | Δ | ○ | Δ | Δ | Δ |
| | Stickiness after application | Δ | Δ | Δ | Δ | Δ | X | X |
| | Form of emulsion | W/O | W/O | W/O | W/O | W/O | W/O | W/O |

Figure 2:
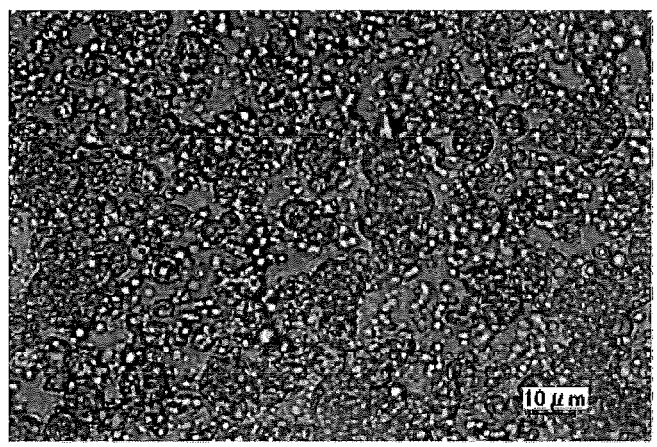
FIG. 2 is a micrograph illustrating a multiphase emulsion of a cream of Example 5.
Figure 3:
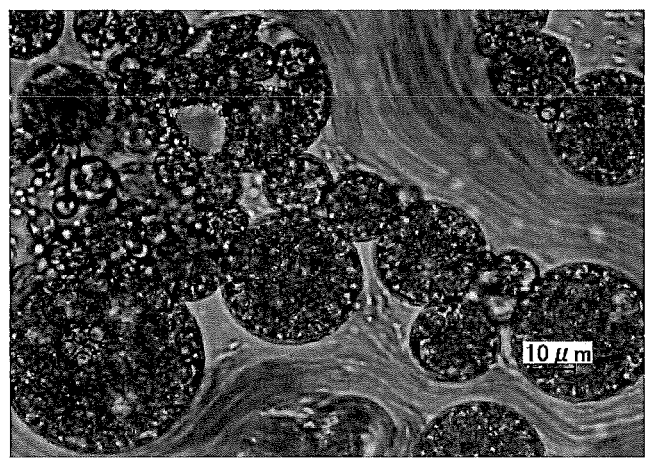
FIG. 3 is a micrograph illustrating a multiphase emulsion of a cream of Example 7.

*1 KF-6017, Product from Shin-Etsu Chemical Co., Ltd., polyether-modified silicone
*2 KF-6106, Product from Shin-Etsu Chemical Co., Ltd., polyglycerin-modified silicone
*3 KF-6043, Product from Shin-Etsu Chemical Co., Ltd., polyether-modified silicone
*4 Carbopol 940, Product from Lubrizol Corporation, carboxy vinyl polymer From the above observation, the creams of Examples containing a substance obtained by neutralizing the acid site of acryl silicone with a base (sodium hydroxide, triethanol amine) showed higher temporal emulsification stability, more favorable use as refreshing feeling, and light spreadability while preventing stickiness than the creams of Comparative Examples. FIG. 1 is a micrograph illustrating a W/O emulsion of Example 1, FIG. 2 is a micrograph illustrating a multiphase emulsion of Example 5, and FIG. 3 is a micrograph illustrating a multiphase emulsion of Example 7.

Examples 8 to 10, and Comparative Examples 8 to 10

The following water-in-oil liquid foundations were prepared according to a conventional method. The liquid foundations obtained were evaluated according to the following method. The results are shown in the following table.

[Evaluation Method]
The emulsification stability of the liquid foundation at 50° C. 3 months later was visually evaluated. The evaluation criteria are shown as follows.
◎: Not separated
○: Slightly separated in upper layer
Δ: Upper layer separated
x: Upper and lower layers separated Then, the liquid foundation prepared (2 g) was applied to the skin for good compatibility, and was evaluated. The uniform hue, non-stickiness, favorable long lasting use, and light spreadability upon application were subjected to sensory evaluation. The results are shown by the following evaluation criteria by the number of panels saying "effective".

[Evaluation Criteria]
◎: "Effective" from 4 to 5 panels
○: "Effective" from 3 panels
Δ: "Effective" from 2 panels
x: "Effective" from 1 panel or none

TABLE 3

| | | Example | | | Comparative Example | | |
|---|---|---|---|---|---|---|---|
| | | 8 | 9 | 10 | 8 | 9 | 10 |
| 1 | Acryl silicone in Synthesis Example 1 | 3 | | | | | |

TABLE 3-continued

|   |   | Example | | | Comparative Example | | |
|---|---|---|---|---|---|---|---|
|   |   | 8 | 9 | 10 | 8 | 9 | 10 |
| 2 | Acryl silicone in Synthesis Example 2 |  | 3 |  |  |  |  |
| 3 | Acryl silicone in Synthesis Example 3 |  |  | 3 |  |  |  |
| 4 | Acryl silicone in Synthesis Example 5 |  |  |  | 3 |  |  |
| 5 | Acryl silicone in Synthesis Example 6 |  |  |  |  | 3 |  |
| 6 | KF-6017 *1 |  |  |  |  |  | 3 |
| 7 | Decamethyl cyclopentasiloxane | 45 | 45 | 45 | 45 | 45 | 45 |
| 8 | Dimethyl polysiloxane (6 mm²/s) | 5 | 5 | 5 | 5 | 5 | 5 |
| 9 | Octadecyl dimethylbenzyl ammonium salt-modified montmorillonite | 4 | 4 | 4 | 4 | 4 | 4 |
| 10 | Hydrophobized titanium oxide *2 | 10 | 10 | 10 | 10 | 10 | 10 |
| 11 | Hydrophobized talc *2 | 6 | 6 | 6 | 6 | 6 | 6 |
| 12 | Hydrophobized mica *2 | 6 | 6 | 6 | 6 | 6 | 6 |
| 13 | Hydrophobized colcothar *2 | 1.5 | 1.5 | 1.5 | 1.5 | 1.5 | 1.5 |
| 14 | Hydrophobized black iron oxide *2 | 0.7 | 0.7 | 0.7 | 0.7 | 0.7 | 0.7 |
| 15 | Hydrophobized yellow iron oxide *2 | 0.2 | 0.2 | 0.2 | 0.2 | 0.2 | 0.2 |
| 16 | Dipropylene glycol | 5 | 5 | 5 | 5 | 5 | 5 |
| 17 | Potassium hydroxide | 0.2 | 0.2 | 0.2 | 0.2 | 0.2 | 0.2 |
| 18 | Fragrance | Appropriate | Appropriate | Appropriate | Appropriate | Appropriate | Appropriate |
| 19 | Purified water | Remainder | Remainder | Remainder | Remainder | Remainder | Remainder |
| Evaluation | Emulsification stability at 50° 3 months later | ◎ | ◎ | ◎ | Δ | Δ | ○ |
|  | Uniform hue | ○ | ○ | ○ | Δ | Δ | ○ |
|  | Non-stickiness | ◎ | ○ | ◎ | Δ | ○ | X |
|  | Long lasting use | ◎ | ○ | ◎ | X | Δ | Δ |
|  | Light spreadability upon application | ○ | ○ | ◎ | Δ | Δ | X |

*1 KF-6017, Product from Shin-Etsu Chemical Co., Ltd., polyether-modified silicone
*2 Hydrophobized: Heated after adding 2% methylhydrogen polysiloxane to powder From the above observation, the liquid foundations of Examples containing a substance obtained by neutralizing the acid site of an acryl silicone with a base showed more favorable temporal emulsification stability, more uniform hue, more favorable powder dispersion stability, non-stickiness, more excellent long lasting use, and more favorable light spreadability than the liquid foundations of Comparative Examples.

It must be stated here that the present invention is not restricted to the embodiments shown by Examples. The embodiments shown by Examples are merely examples so that any embodiments composed of substantially the same technical concept as disclosed in the claims of the present invention and expressing a similar effect are included in the technical scope of the present invention.

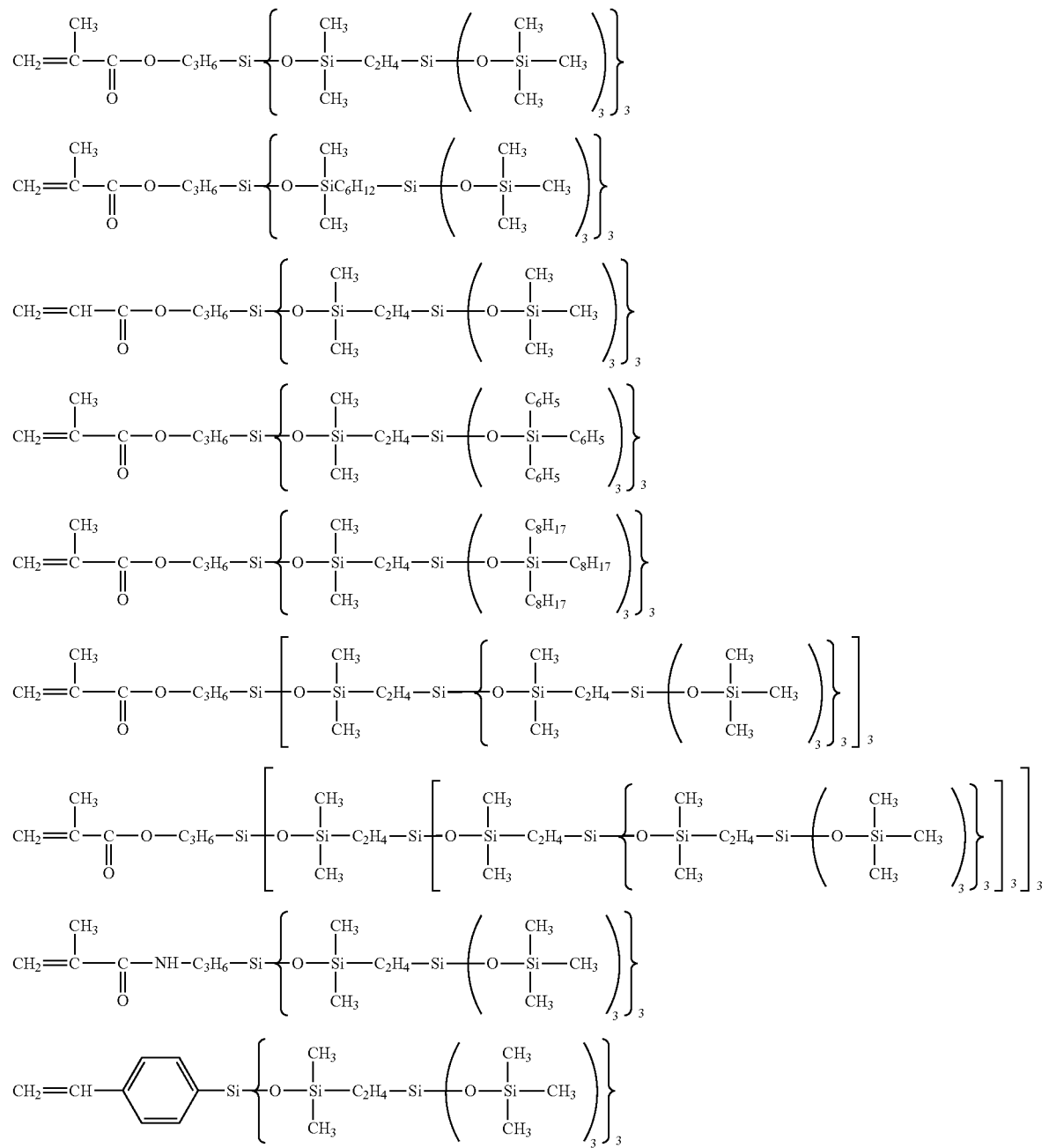

-continued
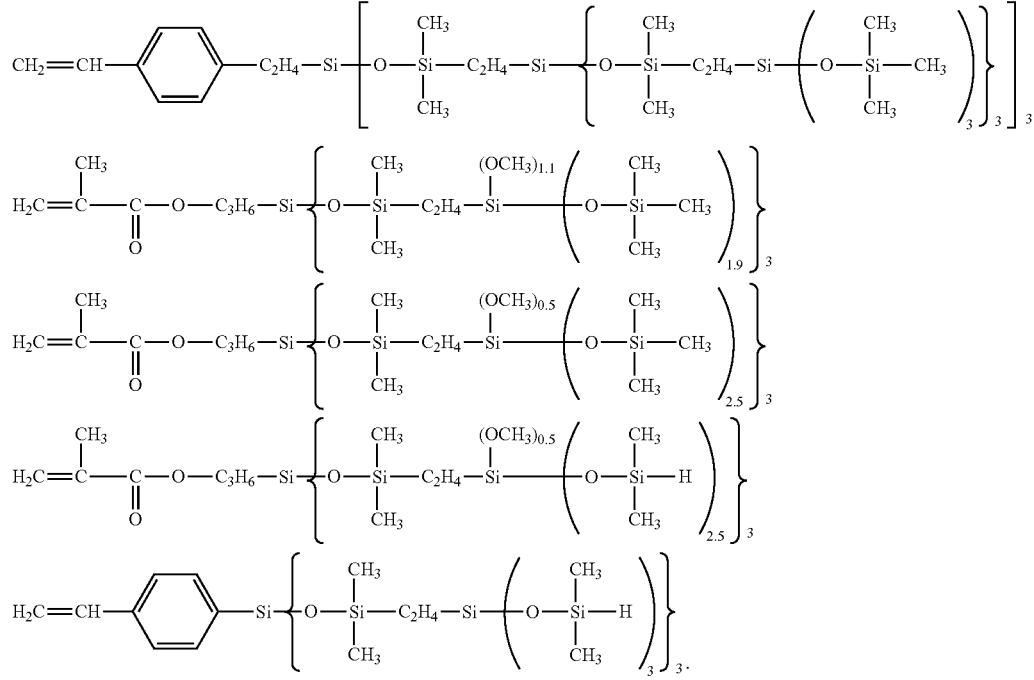
18. The emulsified cosmetic according to claim 2, wherein the silicone dendron group-containing polymerizable monomer is selected from the following formulae,
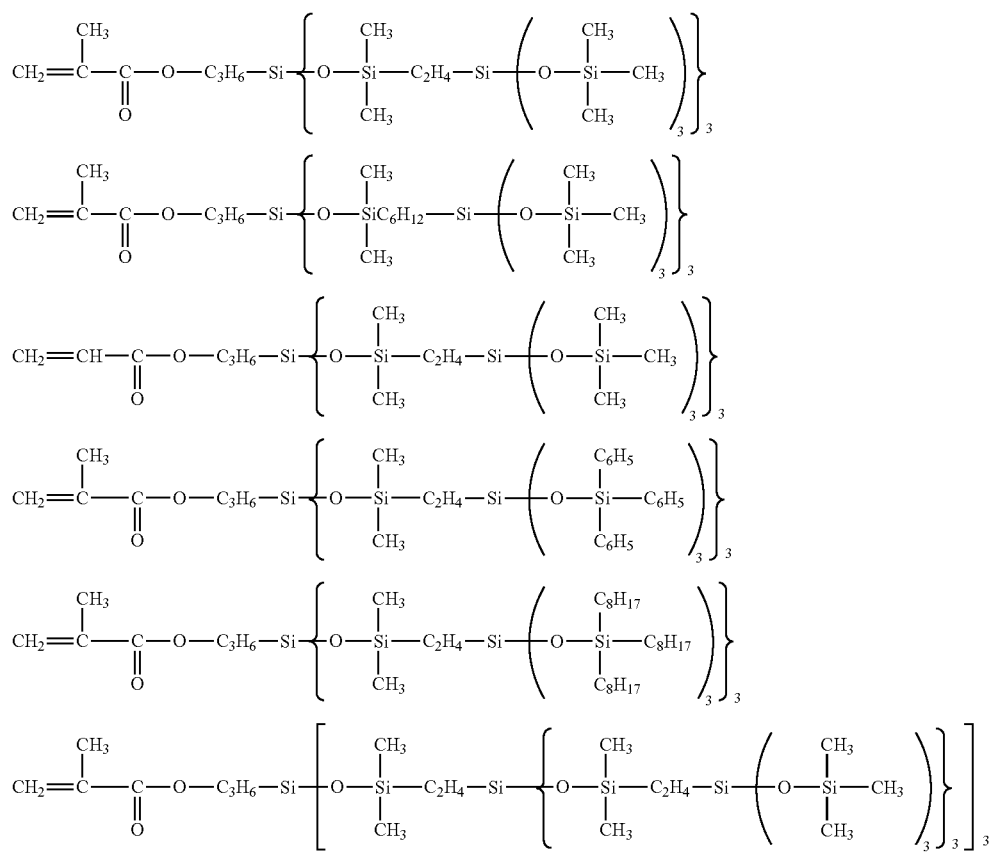

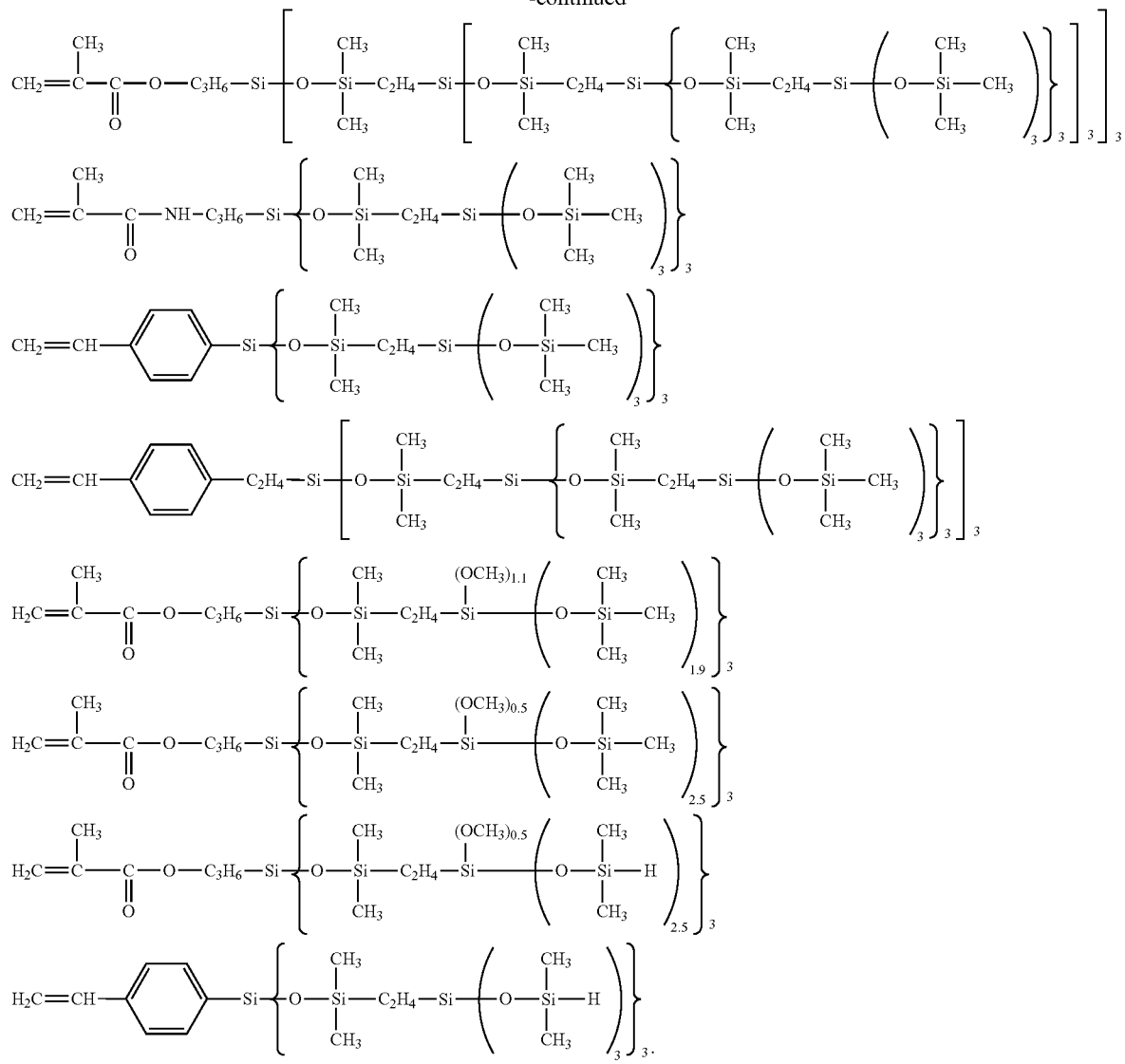
19. The emulsified cosmetic according to claim 3, wherein the silicone dendron group-containing polymerizable monomer is selected from the following formulae,
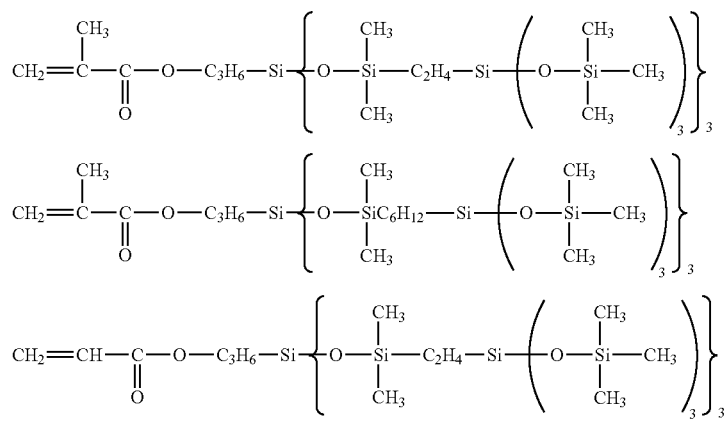

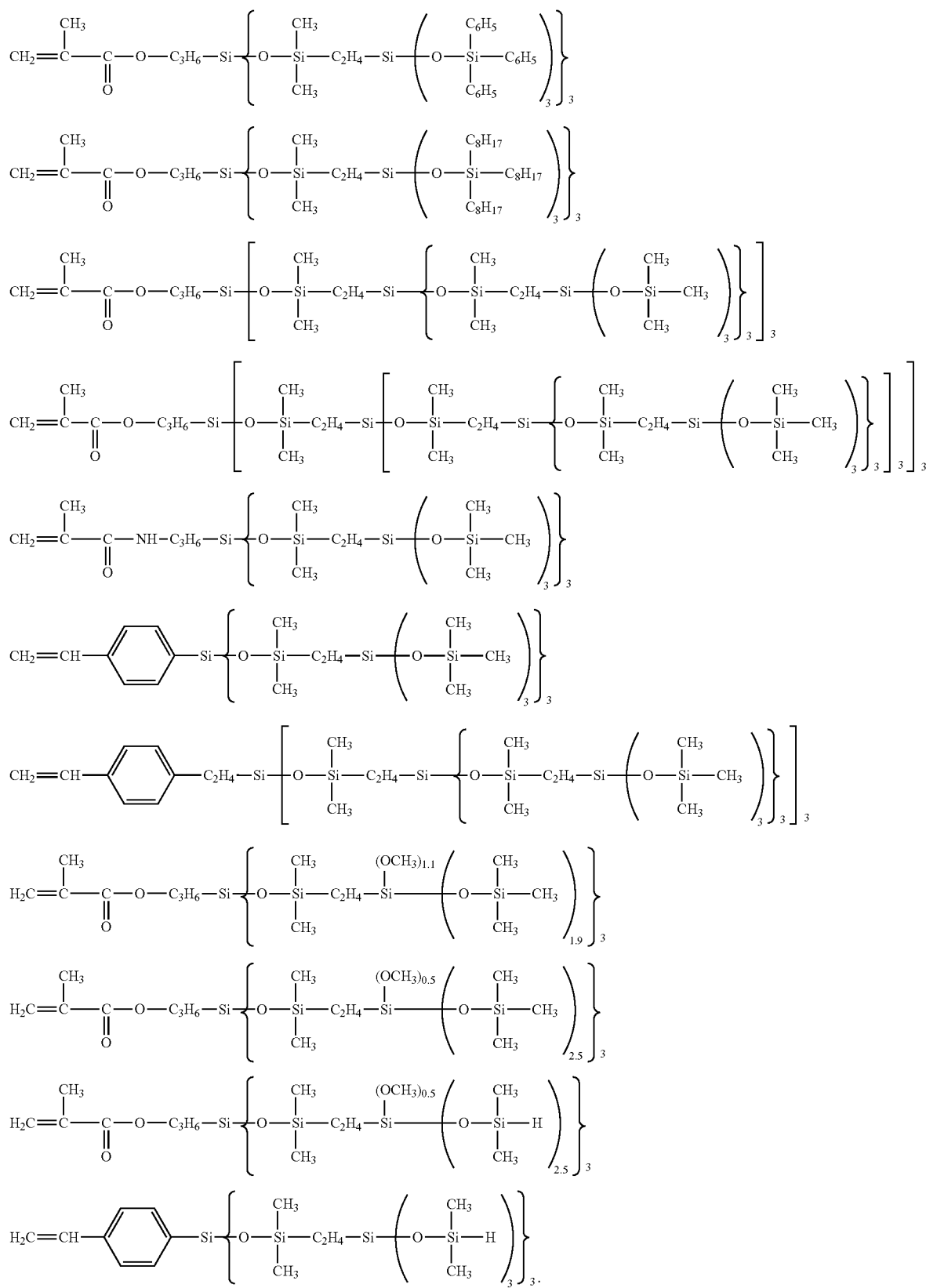

20. The emulsified cosmetic according to claim 4, wherein the silicone dendron group-containing polymerizable monomer is selected from the following formulae,
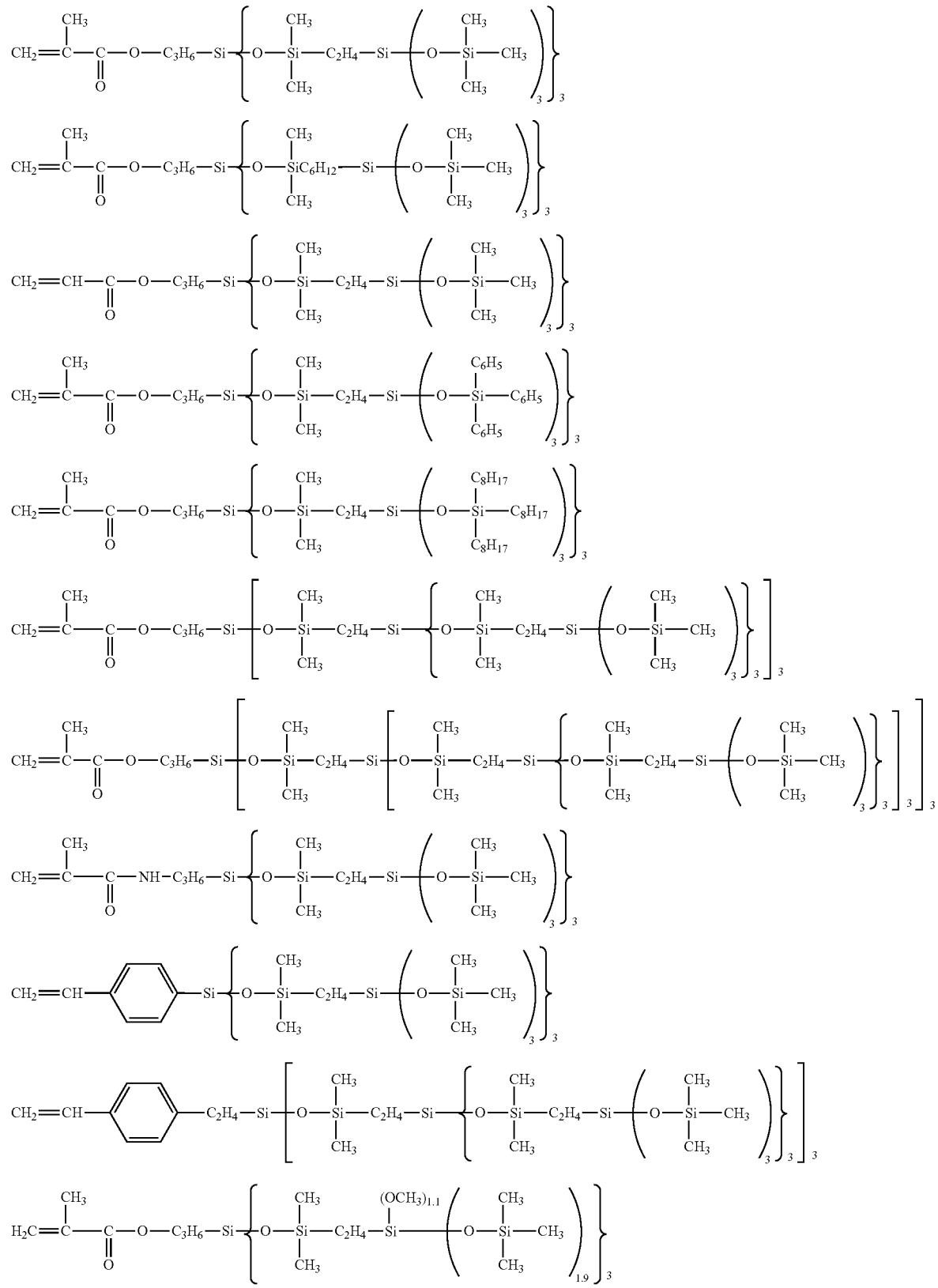

-continued
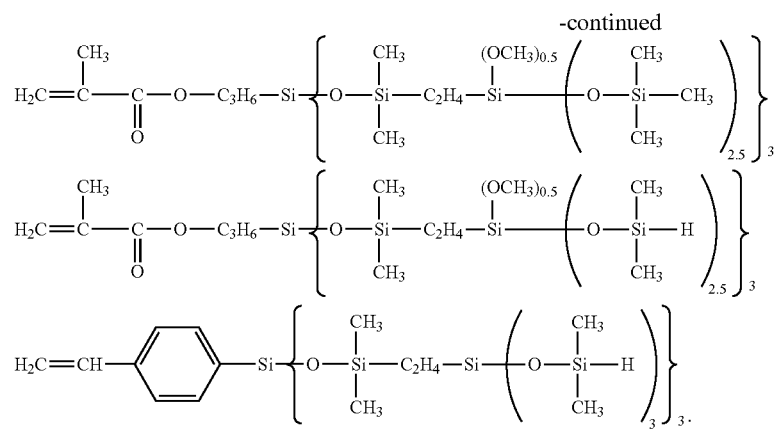

The invention claimed is:

1. An emulsified cosmetic comprising:
an anionic acryl silicone copolymer (A) having an acryl chain as the backbone of the copolymer, the copolymer comprising, as monomer units, the following (I) and (II)
   (I) 1 to 30% by mass of a polymerizable hydrophilic monomer having phosphoric acid, or sulfonic acid neutralized with a base, and
   (II) 10% by mass or more of a silicone macromonomer represented by the following general formula (1), or a silicone dendron group-containing polymerizable monomer,

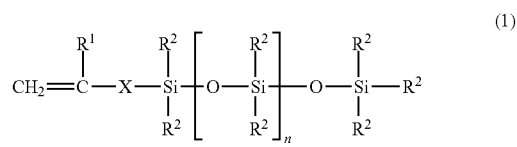

(1)

wherein, X represents a divalent aromatic group having 6 to 12 carbon atoms or $—COOR^3—$; $R^3$ represents an aliphatic group that is bonded to Si; $R^1$ represents a hydrogen atom or a methyl group; $R^2$ represents the same or different fluorine-substituted or unsubstituted monovalent alkyl group having 1 to 30 carbon atoms or aryl group; and "n" represents an integer of 1 to 100;
an oil material (B); and
water (C).

2. The emulsified cosmetic according to claim 1, wherein the oil material (B) is a silicone oil.

3. The emulsified cosmetic according to claim 1, wherein the oil material (B) is a polar oil.

4. The emulsified cosmetic according to claim 3, wherein the emulsified cosmetic is in the form of a multiphase emulsion.

5. The emulsified cosmetic according to claim 1, further comprising an aqueous system thickener (D).

6. The emulsified cosmetic according to claim 2, further comprising an aqueous system thickener (D).

7. The emulsified cosmetic according to claim 3, further comprising an aqueous system thickener (D).

8. The emulsified cosmetic according to claim 4, further comprising an aqueous system thickener (D).

9. The emulsified cosmetic according to claim 1, further comprising a surfactant (E) other than the component (A).

10. The emulsified cosmetic according to claim 2, further comprising a surfactant (E) other than the component (A).

11. The emulsified cosmetic according to claim 3, further comprising a surfactant (E) other than the component (A).

12. The emulsified cosmetic according to claim 4, further comprising a surfactant (E) other than the component (A).

13. The emulsified cosmetic according to claim 5, further comprising a surfactant (E) other than the component (A).

14. The emulsified cosmetic according to claim 6, further comprising a surfactant (E) other than the component (A).

15. The emulsified cosmetic according to claim 7, further comprising a surfactant (E) other than the component (A).

16. The emulsified cosmetic according to claim 8, further comprising a surfactant (E) other than the component (A).

17. The emulsified cosmetic according to claim 1, wherein the silicone dendron group-containing polymerizable monomer is selected from the following formulae,